United States Patent [19]

Shibanuma et al.

[11] Patent Number: 4,690,921

[45] Date of Patent: Sep. 1, 1987

[54] CEPHALOSPORIN COMPOUNDS AND SALTS THEREOF

[75] Inventors: Tadao Shibanuma; Noriaki Nagano, both of Saitama; Ryuichiro Hara, Tokyo; Kohji Nakano, Saitama; Akio Koda; Atsuki Yamazaki, both of Tokyo; Yukiyasu Murakami, Saitama, all of Japan

[73] Assignee: Yamanouchi Pharmaceutical Co., Ltd., Tokyo, Japan

[21] Appl. No.: 656,162

[22] Filed: Sep. 28, 1984

[30] Foreign Application Priority Data

Oct. 11, 1983 [JP] Japan ................. 58-189555
Nov. 18, 1983 [JP] Japan ................. 58-217170
Dec. 26, 1983 [JP] Japan ................. 58-248929
Feb. 15, 1984 [JP] Japan ................. 59-26793
Feb. 28, 1984 [JP] Japan ................. 59-37019
Mar. 7, 1984 [JP] Japan ................. 59-41992

[51] Int. Cl.$^4$ ................. C07D 501/34; A61K 31/545
[52] U.S. Cl. ................. 514/205; 540/225; 514/206
[58] Field of Search ................. 544/29, 25; 424/246; 546/26, 27; 514/205; 540/225

[56] References Cited

U.S. PATENT DOCUMENTS

| 4,200,575 | 4/1980 | Numatu et al. ................. 540/225 |
| 4,278,793 | 7/1981 | Dürckheimer et al. ........... 544/22 |
| 4,331,665 | 5/1982 | Teraji et al. ................. 544/25 |
| 4,470,983 | 9/1984 | Blumbach et al. ............. 546/27 |

FOREIGN PATENT DOCUMENTS 0074645 3/1983 European Pat. Off. .
0088320 9/1983 European Pat. Off. .
0095329 11/1983 European Pat. Off. .

*Primary Examiner*—Nicholas S. Rizzo
*Attorney, Agent, or Firm*—Burgess, Ryan and Wayne

[57] ABSTRACT

Novel cephalosporin compounds of the formula

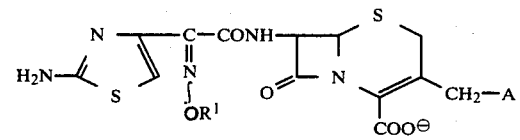

wherein the wavy line means syn-form and anti-form bonds, $R^1$ represents a cyanomethyl group, a thiocarbamoylmethyl group or an aminothiazolylmethyl group, and A represents a unsubstituted or substituted pyridinio group; and salts thereof. These compounds have excellent antibacterial activities.

9 Claims, No Drawings

CEPHALOSPORIN COMPOUNDS AND SALTS THEREOF

BACKGROUND OF THE INVENTION AND THE PRIOR ART

Many 3-substituted cephalosporin compounds having a substituted oxyimino moiety in the 7-position substituent are known as described in, for example, GB Pat. No. 2098216, EP Pat. No. 74645, etc. Some compounds of the invention of the former patent have a characteristic in that the substituent of the 3-position is a pyridinio group which may be substituted by an alkyl group or an alkoxy group, and the oxyimino moiety at the 7-position is substituted by a $C_1$ to $C_6$ alkyl group, etc.; and the invention of the latter patent has a characteristic in that the substituent at the 3-position is a pyridinio group which is substituted by an amino group or a protected amino group, and the oxyimino moiety at the 7-position has a lower aliphatic hydrocarbon group which may be substituted by some group(s).

On the other hand, the present invention provides cephalosporin compounds having a chemical-structural characteristic in that the substituent at the 3-position is a substituted pyridinio group.

DETAILED DESCRIPTION OF THE INVENTION

This invention relates to antibacterial cephalosporin compounds, to the production of these compounds, medical compositions containing them, and salts thereof.

The compounds of this invention are those of the general formula (I) and salts thereof:

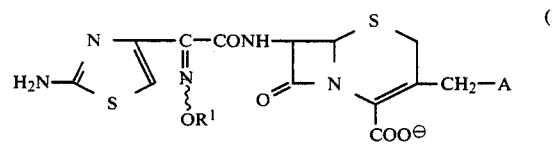

wherein the wavy line means syn-form and anti-form bonds, $R^1$ represents a cyanomethyl group, a thiocarbamoylmethyl group or an aminothiazolylmethyl group, and A represents

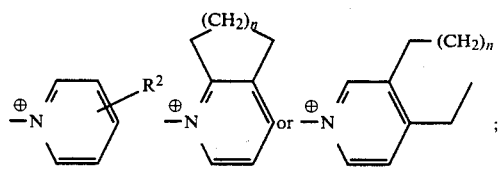

in the above formulas, n represents an integer of 1 to 2, $R^2$ represents a hydrogen atom, a sulfo group, $-(CH_2)_mCOOH$, $-(CH_2)_mOH$, $-(CH_2)_mNHR^3$, or $-CONHR^4$; in these formula, m represents 0 or an integer of 1 to 3, $R^3$ represents a hydrogen atom or an acyl group, and $R^4$ represents a carboxy lower alkyl group of a hydroxyl group.

Examples of "acyl group" are in the foregoing definition of general formula I are a carboxylic acid residue such as a formyl group, an acetyl group, a propionyl group, an oxalo group (HOOC—CO—); etc.

The term "lower" in the foregoing definition of general formula I means a straight or branched carbon chain having 1 to 4 carbon atoms. Thus examples of the "lower alkyl" are methyl, ethyl, isopropyl, butyl, isobutyl, tert-butyl, etc.

Substituent ($R^2$) on the substituted pyridinio group

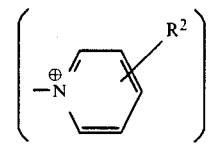

in the above formula I may exist at any position of the pyridinio group.

The salts of the cephem compounds shown by general formula I are the pharmaceutically acceptable nontoxic salts of the cephem compounds and examples of these salts of inorganic bases (e.g. of an alkali metal such as sodium or potassium or of an alkaline earth metal such as calcium or magnesium); ammonium salts; salts of organic bases such as trimethylamine, triethylamine, cyclohexylamine, dicyclohexylamine, diethanolamine, or basic amino acids such as arginine and lysine; salts of inorganic acids such as hydrochloric acid, sulfuric acid, phosphoric acid; and salts of organic acids such as acetic acid, trifluoroacetic acid, lactic acid, tartaric acid, fumaric acid, maleic acid, methanesulfonic acid, ethanesulfonic acid.

The compounds of this invention shown by formula I with an iminoether-type oxime and 2-substituted thiazol group include geometrical isomers and tautomers; this invention includes all these syn-form and anti-form geometrical isomers and mutual tautomers.

The compounds of this invention shown by formula I show antibacterial activities to various pathogens including several important gram positive and negative pathogens. Thus the compounds of this invention are useful for medicaments (especially, antibacterial agent), additives for feeds, preservatives, etc.

Antibacterial activities (minimum effective inhibitory concentrations) of the compounds of the formula I (taked from the following Examples) are shown in the following Table.

TABLE

| | (minimum effective inhibitory concentrations γ/ml) | | | | |
|---|---|---|---|---|---|
| | Example No. | | | | |
| Strain | 7 | 8 | 13 | 17 | 21 |
| Staph. aureus ATCC 6538P | 0.78 | 0.78 | 0.78 | 1.56 | 0.78 |
| Staph. epidermidis IID 866 | ≦0.2 | ≦0.2 | 0.2 | 0.39 | 0.2 |
| E. coli NIHJ | ≦0.2 | ≦0.2 | 0.025 | 0.025 | 0.025 |
| Kleb. pneumoniae ATCC 10031 | ≦0.2 | ≦0.2 | 0.05 | 0.05 | 0.025 |
| Ps. aeruginosa NCTC 10490 | 0.39 | 0.78 | 0.78 | 1.56 | 0.39 |
| Ser. marcescens NY-10 | ≦0.2 | ≦0.2 | 0.1 | 0.05 | 0.025 |

Antibacterial medicants containing compounds according to the invention may be prepared by conventional methods using conventional carriers or excipients. They may for example be administered orally as tablets, pills, capsules, granules; parenterally by intravenous or intramuscular injection; or as suppositories. The appropriate dose is determined in each case considering factors such as the symptom, age and sex of the patient, but for an adult a daily total of 250 to 3,000 mg is usually administered in one to four doses.

The compounds of this invention can be produced by various processes; typical production processes are explained hereinafter:

Process 1:

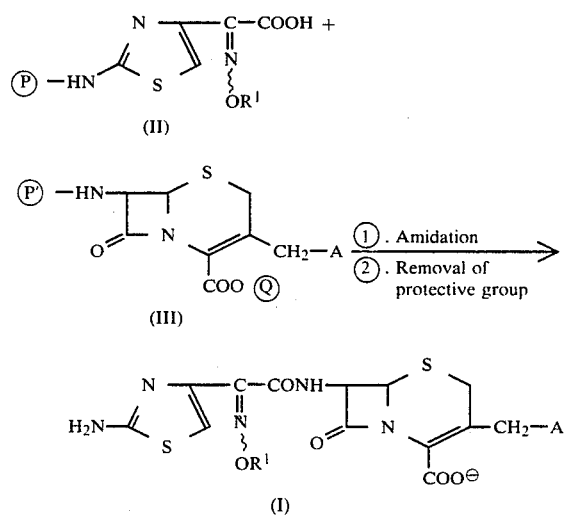

(In the above formulas, Ⓟ is a hydrogen atom or a protective group for an amino group, Ⓟ' is a hydrogen atom or a tri-loweralkylsilyl group, and Ⓠ is a hydrogen atom or a protective group for a carboxyl group; A and R¹ are as defined above; hereunder have the same significances.)

A compound shown by general formula I can thus be produced by reacting a substituted oxyiminothiazolylacetic acid derivative shown by general formula II or a reactive derivative thereof with a 7-amino-3-cephem derivative shown by general formula III and then, if necessary, releasing any protective group(s).

In this case the protective group for an amino group may be one usually used in the field of peptide chemistry and practical examples are acyl groups such as a formyl group, an acetyl group, a propionyl group, a tert-butoxycarbonyl group, a methoxyacetyl group, a methoxypropionyl group, a benzyloxycarbonyl group, a p-nitrobenzyloxycarbonyl group; tri-loweralkylsilyl groups such as a trimethylsilyl group; and aralkyl groups such as a benzyl group, a benzhydryl group (diphenylmethyl group), a trityl group.

Practical examples of the protective group for a carboxy group are those which can be released easily under mild conditions, such as a benzhydryl group, a β-methylsulfonylethyl group, a phenacyl group, a p-methoxybenzyl group, a tert-butyl group, a p-nitrobenzyl group; and lower-alkylsilyl groups such as trimethylsilyl group.

The reaction is usually performed in a solvent under cooling at room temperature or below. Any solvents which do not take part in the reaction can be used. Examples of the solvent usually used are organic solvents such as dioxane, tetrahydrofuran, ether, acetone, ethyl methyl ketone, chloroform, dichloromethane, dichloroethane, methanol, ethanol, acetonitrile, ethyl acetate, ethyl formate, dimethylformamide, dimethyl sulfoxide; these solvents may be used alone or in appropriate combinations.

The compound shown by formula II may be a free carboxylic acid or a reactive derivative thereof. Suitable examples of the compound are mixed acid anhydrides, acid anhydrides, acid halides, active esters, active amide, acid azides. When using the compound in the form of a free carboxylic acid, it is preferred to use a condensing agent such as N,N'-dicyclo-hexylcarbodiimide or N,N'-diethylcarbodiimide.

According to the kind of reactive derivative of carboxylic acid used, it may be preferred for smooth reaction to operate in the presence of a base. Examples of such a base are inorganic bases such as sodium hydrogen-carbonate, potassium hydrogencarbonate, sodium carbonate, potassium carbonate; and organic bases such as trimethylamine, triethylamine, dimethylaniline, pyridine.

The removal of an amino protecting group from the reaction product thus obtained is easily performed, when the group is an aralkyl group (e.g. trityl) or an acyl group, by hydrolysis with acid; and when the group is tri-loweralkylsilyl, by contact with water. As the acid used in this case, formic acid, trifluoroacetic acid, hydrochloric acid, are amongst those preferred. Removal of a carboxy-protecting group is easily performed using an acid in the case of a benzhydryl group, a tert-butyl group, a p-methoxybenzyl group, etc., or by contact with water in the case of tri-loweralkylsilyl such as trimethylsilyl group. Removal of carboxy- and amino-protecting groups can be performed simultaneously.

A salt of the formula I compound can be produced by performing the foregoing production process using a salt of the starting compound, or by applying a salt-forming reaction to the free formula I compound. In the latter case, for example, an alkali metal salt can be produced by adding a n-butanol solution of an alkali 2-ethylhexanoate to the reaction product and then adding thereto an organic solvent having different solubility, such as ether or ethyl acetate; a salt of an organic base or a basic amino acid can be obtained by adding an equivalent amount or a slight excess of organic base or basic amino acid such as dicyclohexylamine, triethylamine, cyclohexylamine, diethanolamine, alginine or lysine to the reaction product; and an ammonium salt can be obtained by adding aqueous ammonia to the reaction product.

The formula I compounds and salts can be separated and purified in ordinary manner, such as extraction with organic solvent, crystallization, column chromatography.

Process 2:

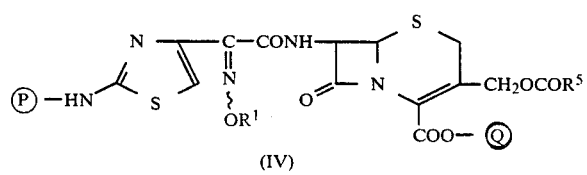

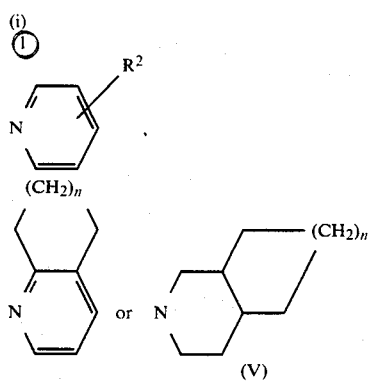

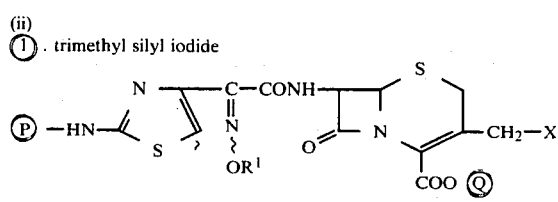

② . Removal of protective group

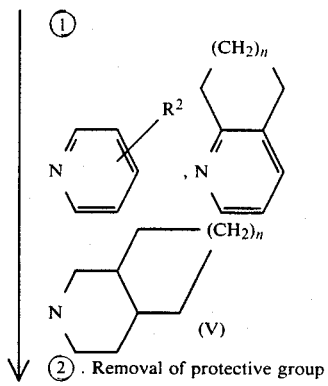

② . Removal of protective group

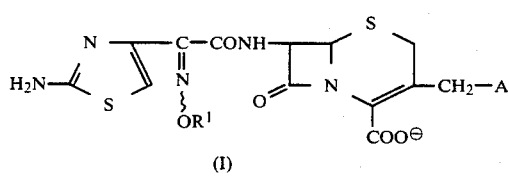

(In the above formulas, R¹, R², Ⓟ, Ⓠ, A, and n are as defined above, R⁵ represents an alkyl group, preferably a lower alkyl group, and X represents a halogen atom. R¹–R⁵ and A hereunder have the same significances as above.)

A compound of formula (I) can thus be produced (i) by reacting a compound of formula (IV) which may have protective group(s) for the amino group and/or the carboxy group, directly with a substituted pyridine compound (V); or (ii) by converting a compound (IV) to the corresponding 3-halogenomethylcephalosporin derivative (VI) and then reacting the compound (VI) with a substituted pyridine compound (V).

This reaction is one for converting the (lower) acyloxy moiety at the 3-position of cephalosporin nucleus (e.g. acetyloxy, propionyloxy, butylyloxy, etc.) into a substituted pyridinio group

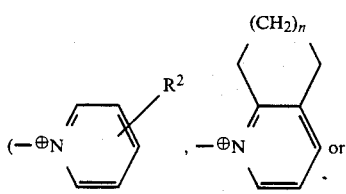

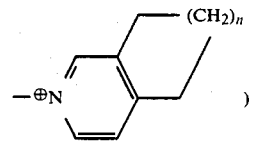

(i) In the case of directly converting the (lower) acyloxy moiety into the pyridinio group, the reaction is usully performed by stirring the compound of formula (IV) or a salt thereof and the compound (V) in water or other inert solvent or a mixture thereof. Examples of the inert solvent used for the purpose are alcohols such as methanol, ethanol; amides such as dimethylformamide, acetamide, and acetones and acetonitriles, etc. For pormoting the reaction, a catalyst such as potassium iodide, potassium bromide, sodium bromide, or potassium thiocyanate may be added to the reaction system in an excessive amount. The reaction easily proceeds at room temperature or under heating.

(ii) In the case of obtaining the desired compound (I) via 3-halogenomethylcephalosporin derivative, the corresponding 3-halogenomethyl derivative (VI) is first obtained, for example, by reacting a compound (IV) (preferably or usually, protected by silyl type group) with trimethylsilyl iodide (TMSI) in an inert solvent such as methylene chloride, chloroform, acetonitrile or acetone; the solvent in the silyl 3-halogenomethyl compound containing solution is distilled away, the concentrate is dissolved in acetonitrile, and excess TMSI is decomposed by adding a small excess of tetrahydrofuran. To the solution thus formed is added the compound of formula (V) (pyridine compound) to provide a silyl derivative of the desired compound.

If desired or necessary, protective group removal and/or salt formation can be effected for the formed compound in the above reaction (i) or (ii). The protective group remomal or salt formation can be effected as previously described.

Process 3:

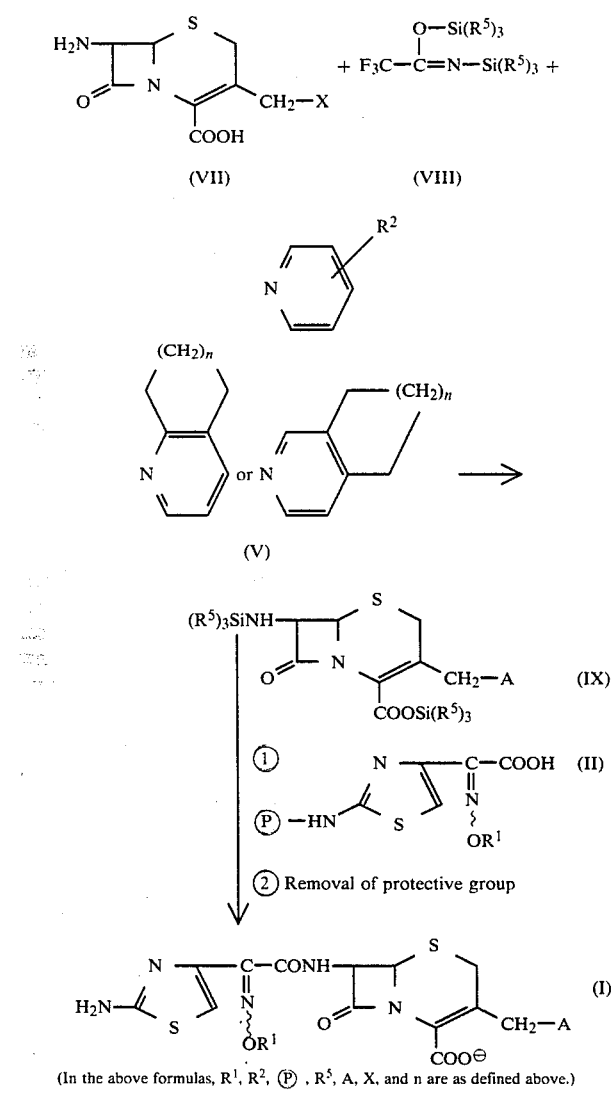

(In the above formulas, $R^1$, $R^2$, Ⓟ , $R^5$, A, X, and n are as defined above.)

In this process, first, 7-amino-3-halogenomethyl-Δ³-cephem-4-carboxylic acid (VII) or a salt thereof is reacted with O,N-bis(tri-lower-alkylsilyl)trifluoroacetamide (VIII) and a substituted pyridine compound of formula (V) in an organic solvent which is inert for the reaction. An amino group, which may exist as a substitute in the pyridine compound (V), may be protected and the protective group may be one usually used in the field of peptide chemistry and practical examples are the foregoing groups Ⓟ for protecting an amino group in the case of process 1. O,N-bis(tri-loweralkylsilyl)trifluoroacetamide (VIII) and a substituted pyridine compound (V) can be reacted simultaneously with the compound (VII). However, it is preferred to react in step by step (2 steps).

The reaction proceeds easily at room temperature. When performing the reaction in 2 steps, the reaction of the 1st step may be performed at room temperature and the 2nd step reaction may be performed under cooling. Thus, the reaction condition may be changed for each step.

Examples of the inert organic solvent usually used are dichloromethane, acetone, acetonitrile, tetrahydrofuran, etc.

Thus, the compound (IX) having protective groups [silyl type groups] is formed.

Then, the reaction solution containing the compound (IX) is reacted with a substituted oxyiminothiazolylacetic acid of formula (II) or a reactive derivative thereof and after removing the protective groups, the desired compound of formula (I) is obtained.

The reaction of the compound (IX) with the compound (II) is usually performed in a solvent under cooling at room temperature or below. Any solvent which does not take part in the reaction can be used. Examples of the solvent are the foregoing organic solvents used in the 1st step and other organic solvents such as dioxane, ether, ethylmethylketone, chloroform, dichloroethane, ethyl acetate, ethyl formate, dimethylformamide, dimethylsulfoxide, etc. These solvents may be used alone or in appropriate combination.

The compound of formula (II) may be a free carboxylic acid or a reactive derivative thereof.

Suitable examples of the derivative are mixed acid anhydrides, acid anhydrides, acid halides, active esters, active amide, acid azides. It is preferred to use acid halides or active esters among them. As the active esters which are preferably used, there are, for example, an ester of 1-hydroxybenzotriazol. When using the compound (II) in the form of a free carboxylic acid, it is preferred to use a condensing agent such as N,N'-dicyclohexylcarbodiimide or N,N'-diethylcarbodiimide.

According to the kind of reactive derivative of carboxylic acid used, it may be preferred for smooth reaction to operate in the presence of a base. Examples of such a base are inorganic bases such as sodium hydrogen-carbonate, potassium hydrogencarbonate, sodium carbonate, potassium carbonate; and organic bases such as trimethylamine, triethylamine, dimethylaniline, pyridine.

The removal of a protective group from the reaction product thus obtained is easily performed, when the group is a tri-loweralkylsilyl group, by treatment with water, and when the group is an aralkyl group (e.g. trityl) or an acyl group, by hydrolysis with acid. The acid used in the latter case, formic acid, trifluoroacetic acid, hydrochloric acid, are amongst those preferred.

A salt of the formula I compound can be produced by performing the foregoing production process using a salt of the starting compound, or by applying a salt-forming reaction ot the free formula I compound.

The formula I compounds and salts can be separated and purified in ordinary manner, such as extraction with organic solvent, crystallization, column chromatography, etc.

Another process:

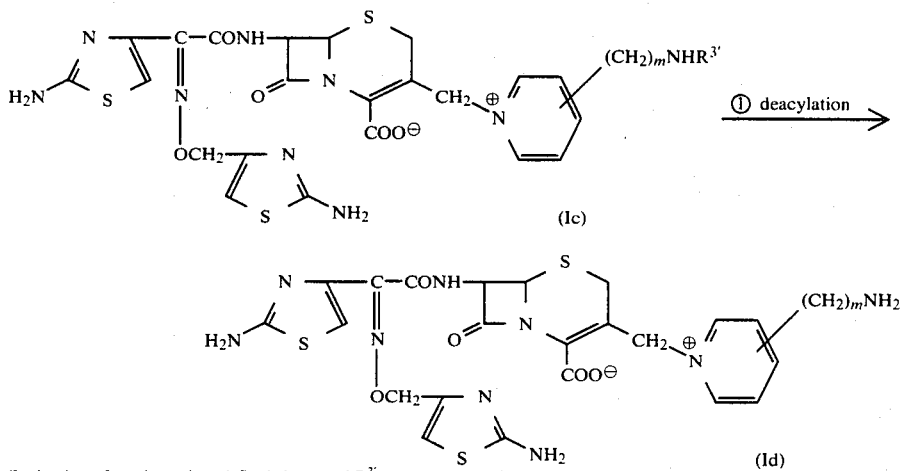

(In the above formulas, m is as defined above, and R³' represents an acyl group.)

The compound of the formula (I$_d$) [that is, the compound of the formula (I) in the case that R¹ is an aminothiazolylmethyl group, and R² is —(CH$_2$)$_m$NHR³; and R³ is a hydrogen atom] can be obtained by deacylating the compound (I$_c$) [that is, the compound of the formula (I) in the case that R¹ is an aminothiazolylmethyl group, and R² is —(CH$_2$)$_m$NHR³; and R³ is an acyl group]. The deacylation reaction can be performed in the same manner as in the removal of the amino protecting group(s) in the foregoing process 1.

REFERENCE EXAMPLE 1

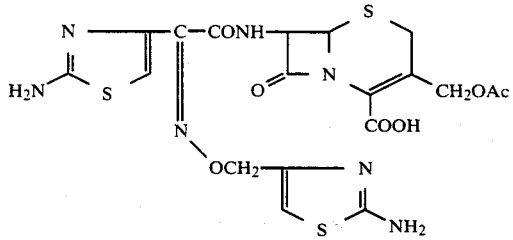

(a). In 12 ml of dichloromethane was suspended 1.566 g of (Z)-α-(2-tritylamino-4-thiazolyl)-α-[(2-tritylamino-4-thiazolyl)methoxyimino]acetic acid and after cooling the suspension to 3° to 4° C. and adding thereto 416 mg of phosphorus pentachloride, the mixture was stirred for 15 minutes at 3° to 4° C. to provide solution A. On the otherhand, 844 mg of 7-amino-3-acetoxymethyl-3-cephem-4-carboxylic acid benzhydryl ester was dissolved in 20 ml of dichloromethane and after cooling the solution to −40° C., 1 g of pyridine was added thereto to provide solution B. Solution A was added dropwise to solution B and the temperature was increased up to −10° C. over a period of 30 minutes. The reaction mixture was poured in 50 ml of ice water and after adjusting the pH thereof to 1 to 2 with 1N hydrochloric acid, the product was extracted with 150 ml of ethyl acetate. The ethyl acetate extract thus obtained was washed with water, dried with anhydrous magnesium sulfate, and concentrated. The residue was subjected to silica gel column chromatography and the product was first eluted with benzene and then a mixture of benzene and ethyl acetate (4:1) and further benzene and ethyl acetate (2:1) to provide 1 g of (Z)-7-{α-(2-tritylamino-4-thiazolyl)-α-[(2-tritylamino-4-thiazolyl)methoxyimino]-acetoamido}-3-acetoxymethyl-3-cephem-4-carboxylic acid benzhydryl ester.

(b). In 4 ml of dichloromethane was dissolved 1 g of (Z)-7-{α-(2-tritylamino-4-thiazolyl)-α-[(2-tritylamino-4-thiazolyl)methoxyimino]acetamido}-3-acetoxymethyl-3-cephem-4-carboxylic acid benzhydryl ester and after adding 0.5 ml of anisole under ice-cooling and then adding 4 ml of trifluoroacetic acid, the resultant mixture was stirred for 20 minutes. The reaction mixture was concentrated and 30 ml of ether and 10 ml of petroleum ether were added to the concentrate to cause solidification. The solids thus formed were collected by filtration, dried, and then dissolved in 16 ml of trifluoroacetic acid under ice-cooling. Then, 6 ml of water was added to the solution and the mixture was stirred for one hour at 20°-23° C. The reaction mixture was concentrated, the residue thus formed was dissolved in 0.5 ml of ethanol and 20 ml of ether was added to the solution to form precipitates, which were collected by filtration, washed with ether, and dried to provide 0.5 g of a ditrifluoroacetate (ditrifluoroacetic acid salt) of (Z)-7-{α-(2-amino-4-thiazolyl)-α-[(2-amino-4-thiazolyl)methoxyimino]acetamido}-3-acetoxymethyl-3-cephem-4-carboxylic acid.

NMR (DMSO—d$_6$):

δ(ppm): 2.03 (3H, —CH$_2$OC—CH$_3$)
                            ‖
                            O 3.51 (2H, 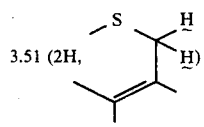)

4.82 (2H, —CH$_2$OC—CH$_3$)
                ‖
                O 4.95 (2H, 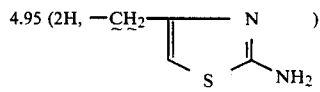 )

5.12 (1H, 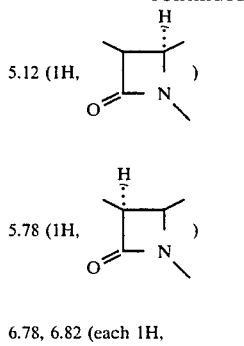)

5.78 (1H, [structure])

6.78, 6.82 (each 1H,

[structures of tautomers with H₂N-C(=N)-S- and -CH₂-])

REFERENCE EXAMPLE 2

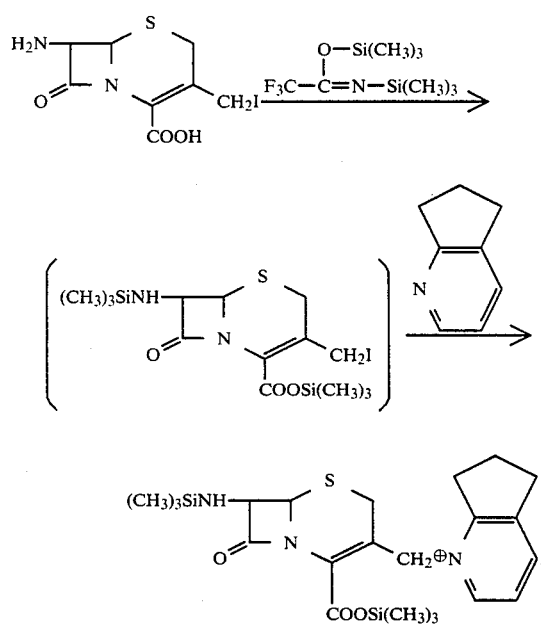

In 50 ml of dichloromethane was suspended 1.7 g of 7-amino-3-iodomethyl-3-cephem-4-carboxylic acid and after therto 2.66 ml of O,N-bis(trimethylsilyl)trifluoroacetamide, the mixture was stirred for 30 minutes at room temperature to provide clear solution. To the solution was added 655 mg of 2,3-cyclopentenopyridine, and the solution was stirred for 4 hours at room temperature to provide a solution containing trimethylsilyl 7-trimethylsilylamino-3-(2,3-cyclopenteno-1-pyridiniomethyl)-3-cephem-4-carboxylate iodide.

REFERENCE EXAMPLE 3

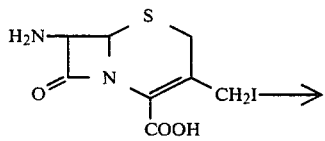

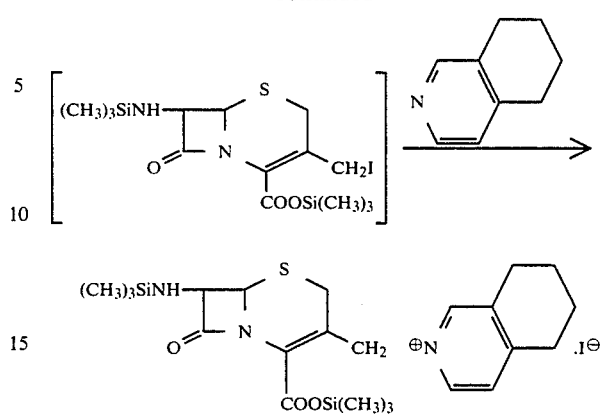

In 50 ml of dichloromethane was suspended 1.7 g of 7-amino-3-iodomethyl-3-cephem-4-carboxylic acid and after adding thereto 2.66 ml of O,N-bis(trimethylsilyl)trifluoroacetamide, the mixture was stirred for 30 minutes at room temperature to provide clear solution. To the solution was added 665 mg of 5,6,7,8-tetrahydroisoquinoline, and the mixture was stirred for 4 hours at room temperature to provide a solution containing trimethylsilyl 7-trimethylsilylamino-3-(5,6,7,8-tetrahydro-2-isoquinoliniomethyl)-3-cephem-4-carboxylate iodide.

REFERENCE EXAMPLE 4

[structures showing (i):
φ₃CNH-C(=N)-S-CH=C(-COOCHφ₂)-N-OH + ClCH₂CN →
φ₃CNH-C(=N)-S-CH=C(-COOCHφ₂)-N-O-CH₂CN]

In 70 ml of dimethylsulfoxide was dissolved 11.9 g (0.02 mole) of (Z)-2-(2-tritylamino-4-thiazolyl)-2-(hydroxyimino)acetic acid benzhydryl ester and after adding thereto 2.76 g of a powder of potassium carbonate and 1.7 g (0.0225 mole) of of chloroacetonitrile, the mixture was allowed to react overnight at room temperature. After the reaction was over, the reaction mixture was poured into 150 ml of ice water, the product was extracted first with 150 ml of ethyl acetate and then with 100 ml of ethyl acetate. The organic layers were collected, and washed twice with 50 ml of water and then with 10 ml of a saturated aqueous sodium chloride solution. The ethyl acetate layer obtained was dried over anhydrous magnesium sulfate, and the solvent was distilled off to provide a caramel. To the caramel was added 100 ml of ethyl ether to powder the caramel. 11.5 g (yield: 90.7%) of (Z)-2-(cyanomethyloxyimino)-2-(2-tritylamino-4-thiazolyl)acetic acid benzhydryl ester was obtained.

IR $\nu_{max}^{KBr}$ cm$^{-1}$:
3330, 1730, 1525, 1245, 1165, 1015, 735, 690
NMR (CDCl₃)
δ (ppm):

-continued 4.72 (1H, s, —CH$_2$—)

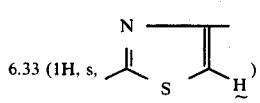

6.33 (1H, s, )

6.85 (1H, s, —CH$\phi_2$)

7.2~7.3 (25H, 5$\phi$)

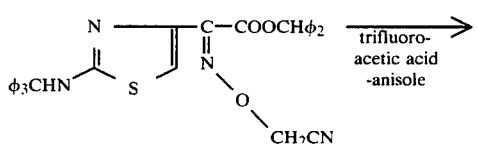

(ii)

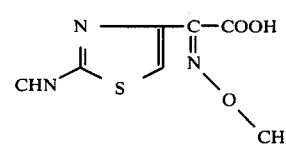

11.3 g (17.8 millimole) of the foregoing compound was dissolved in 26 ml of dichloromethane and 6.5 ml of anisole, and the solution was cooled at −30° C. 19 ml of trifluoroacetic acid was added dropwise to the solution below −20° C. Thereafter, the reaction was performed for 1 hour at −19~−21° C. The reaction solution was distilled off under reduced pressure at low temperature. To the oily residue thus formed was added 150 ml of ether-n-hexane (1:3) to powder the residue. 6.6 g of (Z)-2-(cyanomethyloxyimino)-2-(2-tritylamino-4-thiazolyl)acetic acid was obtained.

IR $\nu_{max}^{KBr}$ cm$^{-1}$;
2900~3100, 1590, 1565, 1190, 695
NMR (d$_6$-DMSO )
δ (ppm);

5.05 (2H, s, —CH$_2$—)

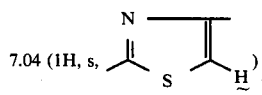

7.04 (1H, s, )

7.2~7.5 (15H, 3$\phi$)
8.94 (1H, s, —NH—)

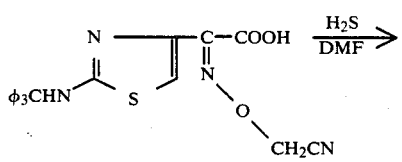

(iii)

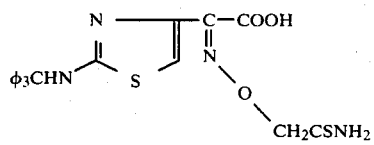

In 20 ml of N,N-dimethylformamide was dissolved 2.814 g (6 millimole) of the foregoing compound and after adding thereto 1.6 ml of triethylamine, the mixture was reacted for 1 hour at 40°–45° C. while passing hydrogen sulfide gas through the mixture. After the reaction was over, hydrogen sulfide was removed by passing nitrogen gas through the reaction mixture at room temperature. The resultant mixture was poured into a solution containing 100 ml of water and 15 ml of 1N-hydrochloric acid solution to form white powder. The powder was collected by filtration, washed with water, and dried to provide 2.11 g of (Z)-2-(thiocarbamoylmethoxyimino)-2-(2-tritylamino-4-thiazolyl)acetic acid.

IR $\nu_{max}^{KBr}$ cm$^{-1}$;

3000~3050, 1560~1590, 1440, 1370, 1265, 1185, 1050, 1030, 965, 830, 730, 695
NMR (d$_6$-DMSO $\phi$)
4.78 (2H, s, —CH$_2$—)

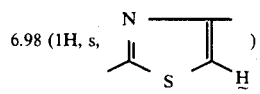

6.98 (1H, s, )

7.2~7.5 (15H, 3$\phi$)

REFERENCE EXAMPLE 5

In 50 ml of dimethylformamide was dissolved 5.6 g of (Z)-α-(2-amino-4-thiazolyl)-α-cyanomethoxyiminoacetic acid, and 7 ml of triethylamine was added thereto.

Hydrogen sulfide gas was passed through the mixture while stirring for 30 minutes. The reaction mixture became green soon. A clear solution was once formed and thereafter crystals were precipitated. Crystals were collected by filtration, and the crystals thus obtained were added to 200 ml of water. After adjusting the pH of the mixture to 3–4 with 6N-hydrochloric acid, the resultant crystals were collected by filtration and dried to provide 4.45 g of (Z)-α-(2-amino-4-thiazolyl)-α-thiocarbamoylmethoxyiminoacetic acid.

NMR (d$^6$-DMSO + CD$_3$OD)
δ(ppm); 4.80 (2H, s, —OCH$_2$)

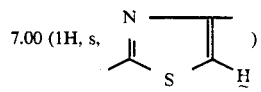

7.00 (1H, s, )

EXAMPLE 1

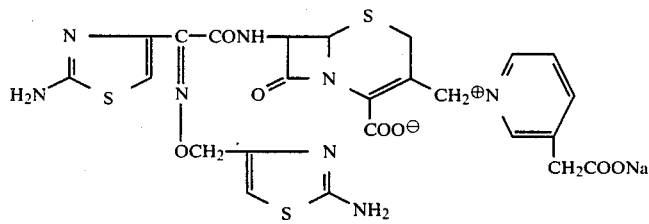

In 7 ml of water were dissolved 7.48 g of potassium iodide, 1.26 g of sodium hydrogencarbonate, 2.55 g of 3-pyridineacetic acid, and 1.087 g of a ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 10 hours at 56°–57° C. The mixture was cooled and subjected to column chromatography on Diaion HP-20 (made by Mitsubishi Chemical Industries Ltd.). The product was eluted first with water and then with mixtures of water and methanol while changing succesively the mixing ratio. The fractions containing the desired product were collected, concentrated, and lyophilized to provide 124 mg of (Z)-7-{α-(2-amino-4-thizolyl)-α-[(2-amino-4-thiazolyl)methoxyimino]acetamido}-3-(3-carboxylatemethyl-1-pyridiniomethyl)-3-cephem-4-carboxylate mono-sodium salt.

NMR (DMSO—d$_6$)
δ(ppm): 3.91, (2H, —CH$_2$COO$^-$)

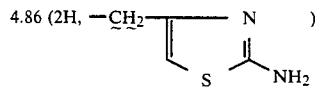

4.86 (2H,

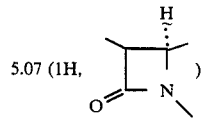

5.07 (1H,

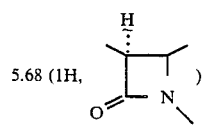

5.68 (1H, 6.40, 6.68 (each 1H,

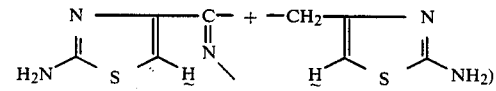

-continued

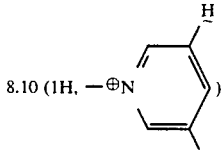

8.10 (1H,

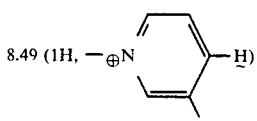

8.49 (1H,

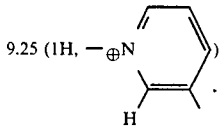

9.25 (1H,

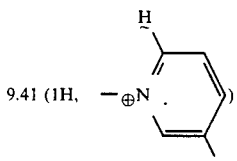

9.41 (1H,

EXAMPLE 2

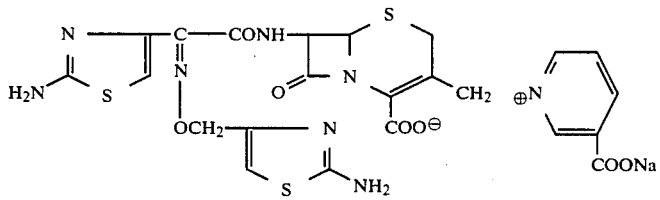

In 7 ml of water were dissolved 7.48 g of potassium iodide, 1.26 g of sodium hydrogencarbonate, 1.845 g of 3-pyridinecarboxylic acid, and 1.087 g of ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 10 hours at 56°–57° C.

The mixture was cooled and subjected to column chromatography on Diaion HP-20 and the product was eluted first with water and then with mixtures of water and methanol while changing succesively the mixing ratio. The fractions containing the desired product were collected, and concentrated, and lyophilized to provide 95 mg of (Z)-7-{α-(2-amino-4-thiazolyl)-α-[(2-amino-4-thiazolyl)-methoxyimino]acetamido}-3-(3-carboxylate-1-pyridiniomethyl)-3-cephem-4-carboxylate mono-sodium salt.

NMR (DMSO—d₆)
δ(ppm): 4.86 (2H, 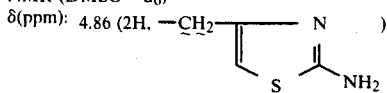)

5.13 (1H, 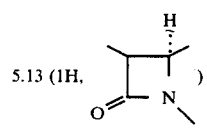)

5.77 (1H, 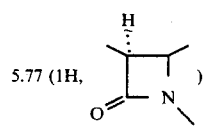)

6.40, 6.69 (each 1H, 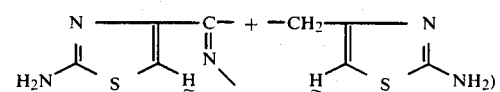)

8.14 (1H, 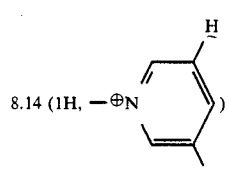)

8.84 (1H, 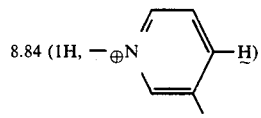)

9.27 (1H, 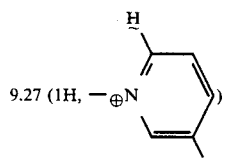)

9.51 (1H, 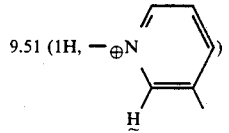)

EXAMPLE 3

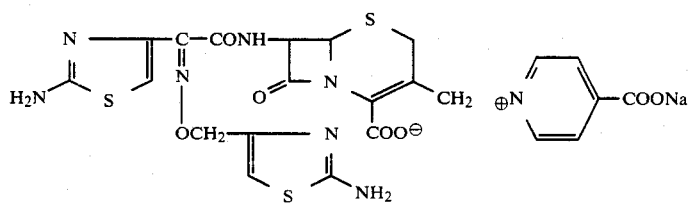

In 7 ml of water were dissolved 7.48 g of potassium iodide, 1.26 g of sodium hydrogencarbonate, 1.845 g of 4-pyridinecarboxylic acid, and 1.087 g of ditrifluoroacetate of (Z)-7-{2-amino-4-thiazolyl)-α-[(2-amino-4-thiazolyl)methoxyimino]acetamido}-3-acetoxymethyl-3-cephem-4-carboxylic acid and the mixture was stirred for 10 hours at 56°-57° C.

The mixture was cooled and subjected to column chromatography on Diaion HP-20 and the product was eluted first with water and then with mixtures of water and methanol while changing succesively the mixing ratio. The fractions containing the desired product were collected, concentrated, and lyophilized to provide 85 mg of (Z)-7-{α-(2-amino-4-thiazolyl)-α-[(2-amino-4-thiazolyl)methoxyimino]acetamido}-3-(4-carboxylate-1-pyridiniomethyl)-3-cephem-4-carboxylate monosodium salt.

NMR (DMSO-d₆)
δ (ppm):

4.87 (2H, 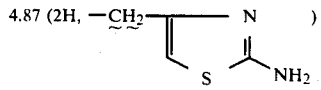)

5.13 (1H, )

5.78 (1H, 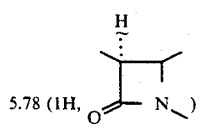)

6.40, 6.69 (each 1H, 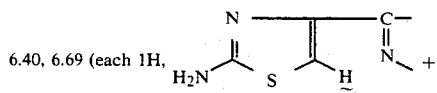 )

8.29 (2H, 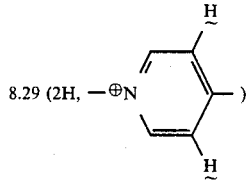)

9.14 (2H, 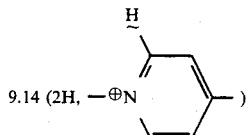)

EXAMPLE 4

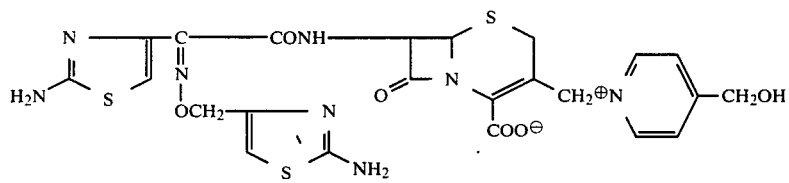

In 7 ml of water were dissolved 7.48 g of potassium iodide, 126 mg of sodium hydrogencarbonate, 1.635 g of 4-pyridinemethanol, and 1.087 g of ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 10 hours at 56°–57° C.

The reaction mixture was cooled and subjected to column chromatography on Diaion HP-20 and the product was eluted first with water and then with mixtures of water and methanol while changing succesively the mixing ratio. The fractions containing the desired product were collected, concentrated, and lyophilized to provide 90 mg of (Z)-7-{α-(2-amino-4-thiazolyl)-α-[(2-amino-4-thiazolyl)-methoxyimino]acetamido}-3-(4-hydroxymethyl-1-pyridiniomethyl)-3-cephem-4-carboxylate.

NMR (DMSO-$d_6$)
δ (ppm):
4.79 (2H, —$\underline{CH_2}$OH)

4.86 (2H, 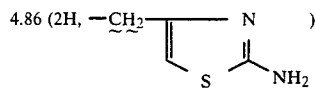)

5.07 (1H, 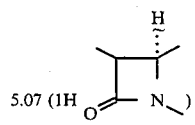)

5.72 (1H, 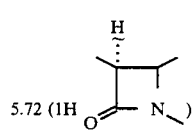)

6.41, 6.69 (each 1H, 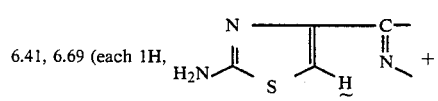

)

8.01 (2H, 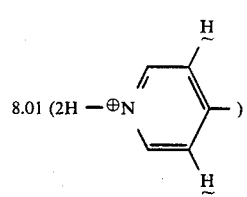)

9.29 (2H, 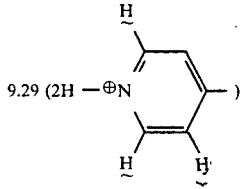)

EXAMPLE 5

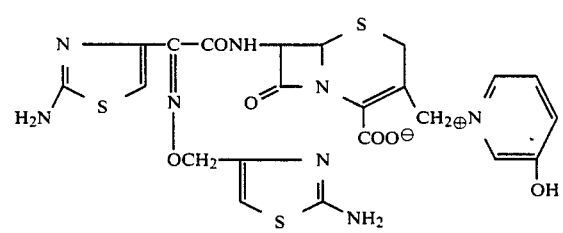

In 7 ml of water were dissolved 7.48 g of potassium iodide, 126 mg of sodium hydrogencarbonate, 1.425 g of 3-hydroxypyridine, and 1.087 g of ditrifluoroacetate of (Z)-7-{α-(2-amino-4-thiazolyl)-α-[(2-amino-4-thiazolyl)-methoxyimino]acetamido}-3-acetoxymethyl-3-cephem-4-carboxlic acid and the mixture was stirred for 12 hours at 56°–58° C.

The reaction mixture was cooled and subjected to column chromatography on Diaion HP-20 and the product was eluted first with water and then with mixtures of water and methanol while changing succesively the mixing ratio. The fractions containing the desired product were collected, concentrated, and lyophilized to provide 63 mg of (Z)-7-{α-(2-amino-4-thiazolyl)-α-[(2-amino-4-thiazolyl)methoxyimino]acetamido}-3-(3-hydroxy-1-pyridiniomethyl)-3-cephem-4-carboxylate.

NMR (DMSO—$d_6$)
δ(ppm):

4.89 (2H, 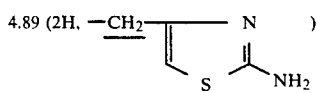)

5.12 (1H, 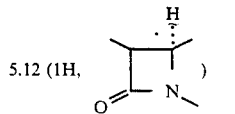)

5.74 (1H, 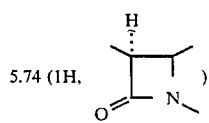)

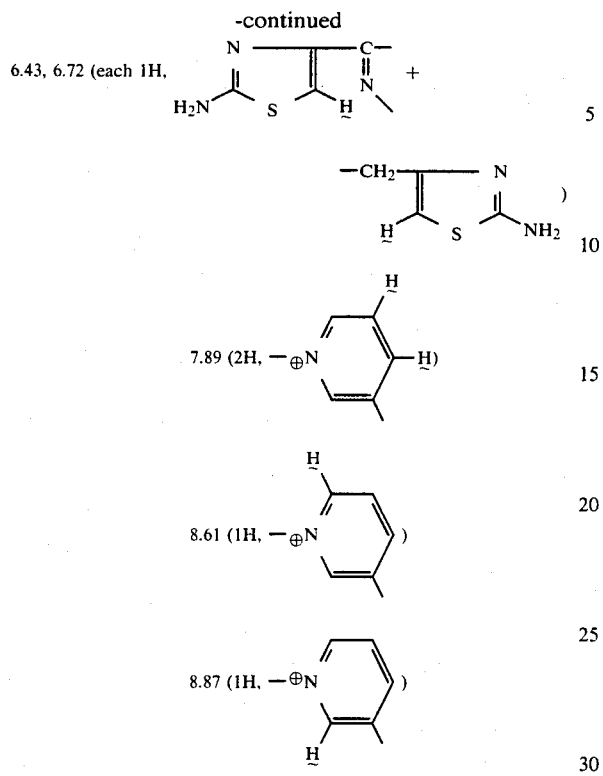
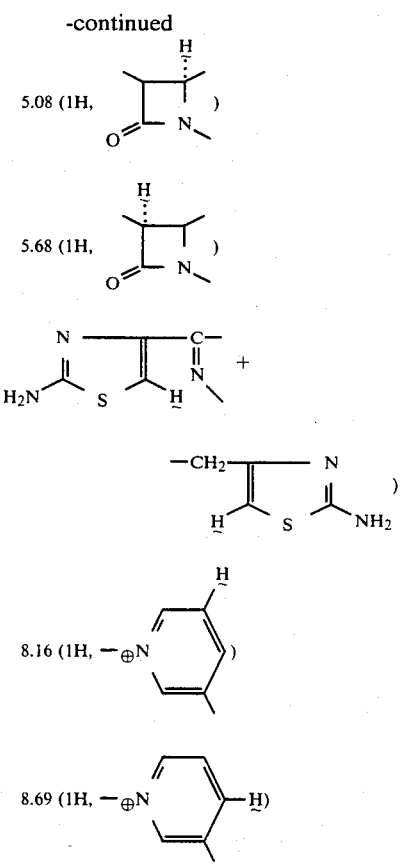

EXAMPLE 6

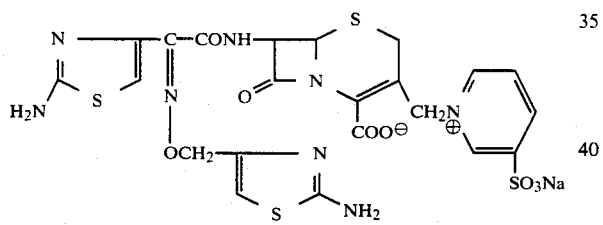

In 7 ml of water were dissolved 7.48 g of potassium iodie, 1.26 g of sodium hydrogencarbonate, 2.38 g of 3-pyridinesulfonic acid, and 1.087 g of ditrifluoroacetate of (Z)-7-{α-(2-amino-4-thiazolyl)-α-[(2-amino-4-thiazolyl)methoxyimino]acetamido}-3 -acetoxymethyl-3-cephem-4-carboxylic acid and the mixture was stirred for 10 hours at 56°–58° C.

The reaction mixture was cooled and subjected to column chromatography on Diaion HP-20 and the product was eluted first with water and then with mixtures of water and methanol while changing succesively the mixing ratio. The fractions containing the desired product were collected, concentrated, and lyophilized to provide 120 mg of (Z)-7-{α-(2-amino-4-thiazolyl)-α-[(2-amino-4-thiazolyl)methoxyimino]acetamido}-3-(3-sulfonate-1-pyridiniomethyl)-3-cephem-4-carboxylate mono-sodium salt.

NMR (DMSO—d₆)

δ(ppm): 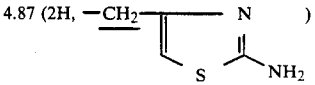

EXAMPLE 7

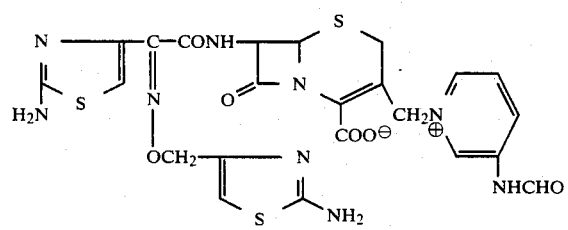

In 7 ml of water were dissolved 7.48 g of sodium iodide, 252 mg of sodium hydrogencarbonate, 1.83 g of 3-formamidopyridine, and 1.087 g of ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the reaction mixture was stirred for 10 hours at 56°–58° C.

The reaction mixture was cooled and subjected to column chromatography on Diaion HP-20 and the product was eluted first with water and then with mixtures of water and methanol while changing succesively the mixing ratio. The fractions containing the desired product were collected, concentrated, and lyophilized to provide 122 mg of (Z)-7-{α-(2-amino-4-thiazolyl)-α-[(2-amino-4-thiazolyl)methoxyimino]acetamido}-3-(3-formamido-1-pyridiniomethyl)-3-cephem-4-carboxylate.

NMR (DMSO—d₆)
δ(ppm): 4.88 (2H, 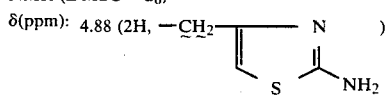 )

5.09 (1H, 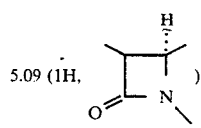 )

5.73 (1H, 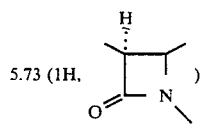 )

6.43, 6.71 (each 1H,

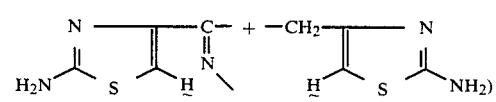)

8.09 (1H, 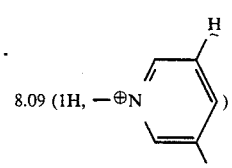 )

8.51 (1H, —NHCHO)

8.70 (1H, 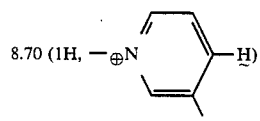)

9.16 (1H, 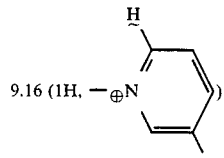)

9.63 (1H, 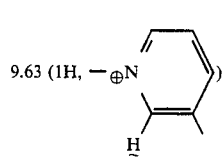)

EXAMPLE 8

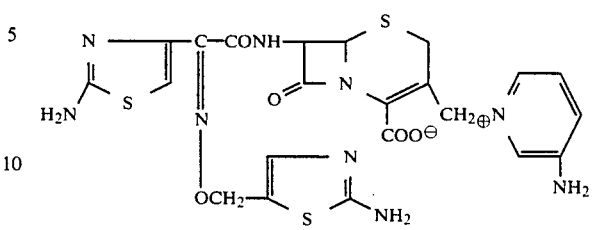

In 6 ml of methanol was suspended 396 mg of (Z)-7-{α-(2-amino-4-thiazolyl)-α-[(2-amino-4-thiazolyl)methoxyimino]acetamido}-3-(3-formamido-1-pyridiniomethyl)-3-cephem-4-carboxylate and after adding thereto 2.6 ml of concentrated hydrochloric acid under ice-cooling, the mixture was stirred for 80 minutes at 20°–23° C.

The reaction mixture was concentrated upto about 3 ml and the concentrate was poured into 300 ml of water. Then, after adjusting the pH of the solution to about 7 with an aqueous sodium hydrogencarbonate solution, the solution was subjected to column chromatography on Diaion HP-20. The product was eluted first with water and then with mixtures of water and methanol while changing succesively the mixing ratio and the fractions containing the desired product were collected, concentrated, and lyophilized to provide 78 mg of (Z)-7-{α-(2-amino-4-thiazolyl)-α-[(2-amino-4-thiazolyl)methoxyimino]acetamido}-3-(3-amino-1-pyridiniomethyl)-3-cephem-4-carboxlate.

NMR (DMSO—d₆)
δ(ppm): 4.91 (2H, 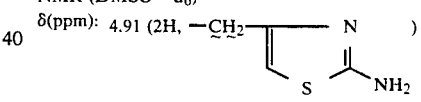 )

5.07 (1H, 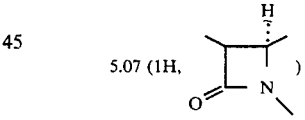 )

5.69 (1H, 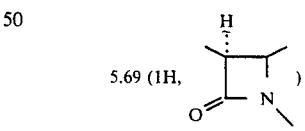 )

6.44, 6.72 (each 1H,

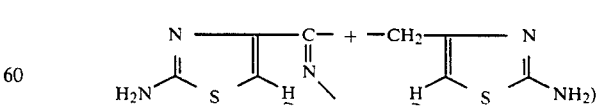)

7.65 (1H, 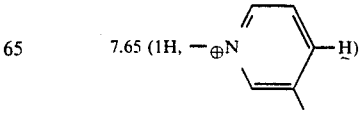)

7.70 (1H, 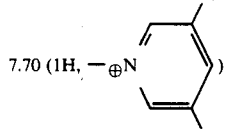)

8.39 (1H, 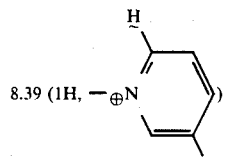)

8.52 (1H, 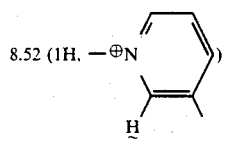)

EXAMPLE 9

5.09 (1H, 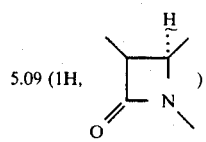)

5.71 (1H, 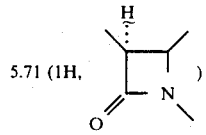)

6.41, 6.70 (each 1H,
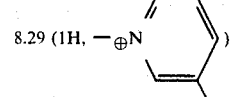)

8.29 (1H, 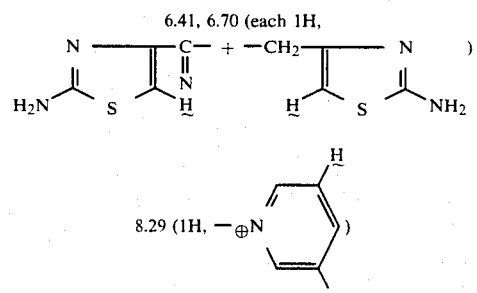)

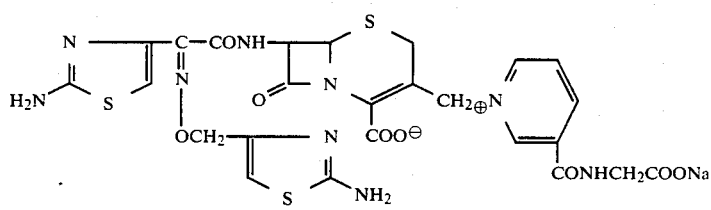

In 7 ml of water were dissolved 7.48 g of sodium iodide, 1.26 g of sodium hydrogencarbonate, 2.7 g of nicotinylglycine, 1.087 g of ditrifluoroacetate of (Z)-7-{α-(2-amino-4-thiazolyl)-α-[(2-amino-4-thiazolyl)-methoxyimino]acetamido}-3-acetoxymethyl-3-cephem-4-carboxylic acid and the mixture was stirred for 10 hours at 58°–59° C.

The reaction mixture was cooled and subjected to column chromatography on Diaion HP-20 and the product was eluted first with water and then mixtures of water and methanol while changing succesively the mixing ratio. The fractions containing the desired product were collected, concentrated, and lyophilized to provide 63 mg of (Z)-7-{α-(2-amino-4-thiazolyl)-α-[(2-amino-4-thiazolyl)methoxyimino]acetamido}-3-{3-[N-(carboxylatemethyl)carbamoyl]-1-pyridiniomethyl}-3-cephem-4-carboxylate mono-sodium salt.

NMR(DMSO—d$_6$) δ(ppm):

3.96 (2H, —CONH.CH$_2$COO$^\ominus$)

4.87 (2H, 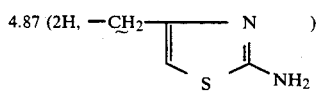)

8.97 (1H, 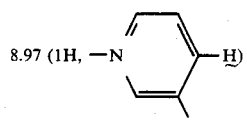)

9.70 (1H, 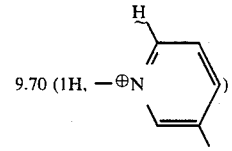)

9.76 (1H, 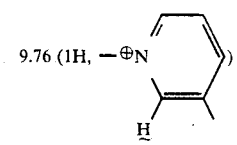)

EXAMPLE 10

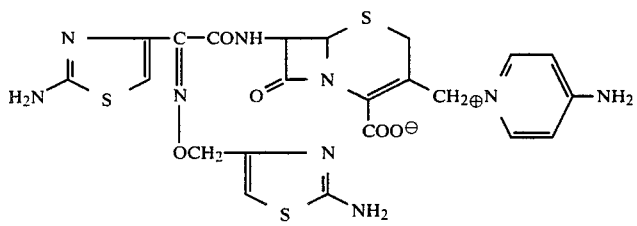

In 7 ml of water were dissolved 7.48 g of sodium iodide, 252 mg of sodium hydrogencarbonate, 1.83 g of 4-formamidopyridine, and 1.087 g of ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 9 hours at 59°–60° C.

The reaction mixture was cooled and subjected to colum chromatography on Diaion HP-20, the product was eluted with water-methanol (7.5:2.5), and lyophilized to provide 115 mg of a crude product. The crude product was suspended in 1.5 mg of methanol and after adding thereto 0.62 ml of concentrated hydrochloric acid under ice-cooling, the mixture was stirred for 1 hour at 20°–23° C. The reaction mixture was concentrated to remove methanol, and the concentrate was poured into 60 ml of water. Then, after adjusting the pH of the solution to 7 with an aqueous sodium hydrogencarbonate solution, the solution was subjected to column chromatography on Diaion HP-20. The product was eluted with water-methanol (7.5:2.5) and concentrated and lyophilized to provide 18 mg of 7-{α-(2-amino-4-thiazolyl)-α-[(2-amino-4-thiazolyl)methox-

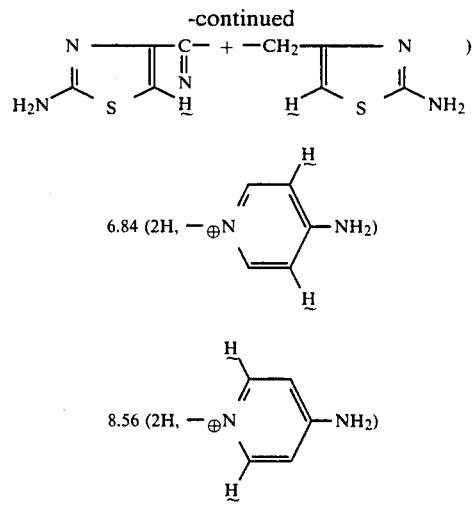

EXAMPLE 11

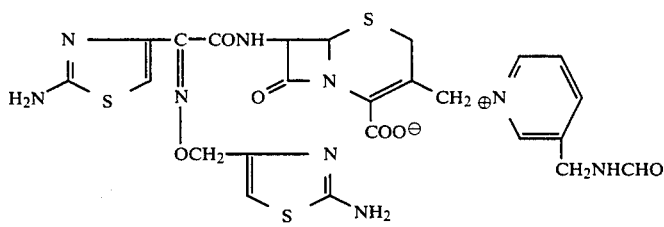

yimino]acetamido}-3-(4-amino-1-pyridiniomethyl)-3-cephem-4-carboxylate.

NMR(DMSO—d$_6$) δ(ppm):

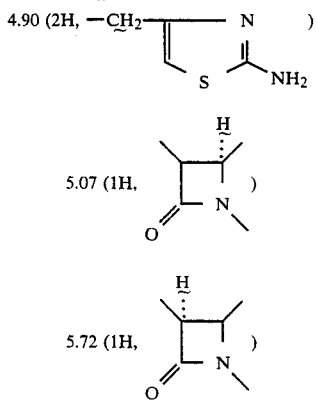

In 7 ml of water were dissolved 7.48 g of potassium iodide, 252 mg of sodium hydrogencarbonate, 2.04 g of 3-formamidomethylpyridine, and 1.087 g of ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and the mixture was stirred for 10 hours at 56°–58° C.

The reaction mixture was cooled and subjected to column chromatography on Diaion HP-20 and the product was eluted first with water and then with mixtures of water and methanol while changing succesively the mixing ratio. The fractions containing the desired product were collected, concentrated, and lyophilized to provide 141 mg of (Z)-7-{α-(2-amino-4-thiazolyl)-α-[(2-amino-4-thiazolyl)methoxyimino]acetamido}-3-(3-formamidomethyl-1-pyridiniomethyl)-3-cephme-4-carboxylate.

NMR (DMSO-d$_6$)

δ(ppm): 4.53 (2H, —CH$_2$NHCHO)

-continued

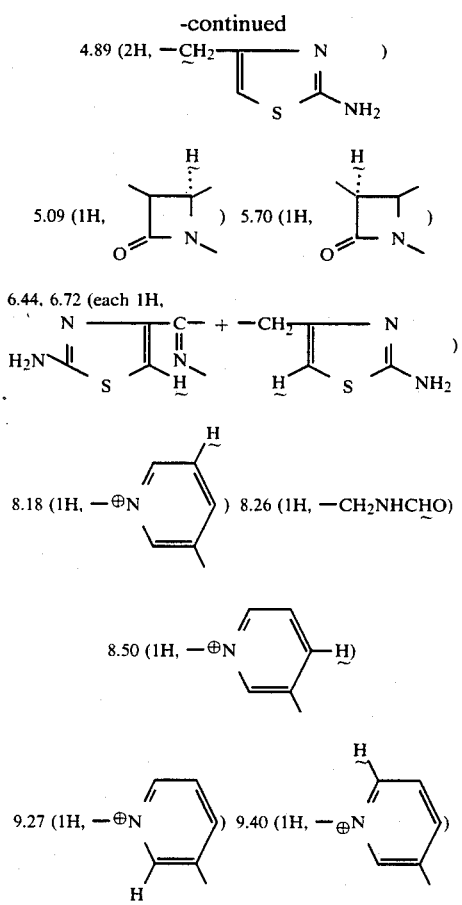

filtration, washed with 30 ml of ether, and dried. The crude product was suspended in water and after adjusting the pH of the suspension to 8–9 with an aqueous solution of sodium hydrogencarbonate, the mixture subjected to column chromatography of Diaion HP-20. The product was eluted first with water and then with mixtures of water and methanol while changing successively the mixing ratio and the fractions containing the desired product were collected, concentrated, and lyophilized to provide 24 mg of (Z)-7-{α-(2-amino-4-thiazolyl)-α-[(2-amino-4-thiazolyl)methoxyimino]acetamido}-3-(4-hydroxycarbamoyl-1-pyridiniomethyl)-3-cephem-4-carboxylate.

NMR (DMSO-$d_6$)

δ(ppm): 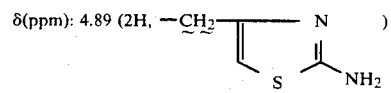
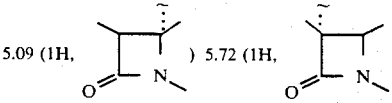
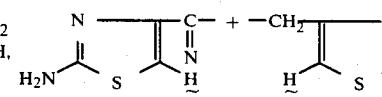
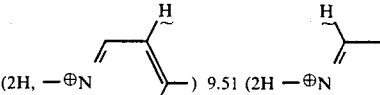
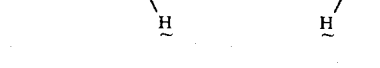

EXAMPLE 12

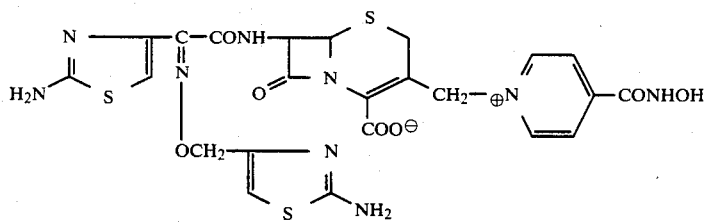

In 4 ml of dichloromethane was suspended 725 mg of ditrifluoroacetate of (Z)-7-{α-(2-amino-4-thiazolyl)-α-[(2-amino-4-thiazolyl)methoxyimino]acetamido}-3-acetoxymethyl-3-cephem-4-carboxylic acid and after adding thereto 875 ml of O,N-bis(trimethylsilyl)trimethylsilyl)trifluoroacetamide, the mixture was stirred for 1 hour at room temperature. To the solution was added 285 ml of trimethylsilyl iodide and after stirring the mixture for 40 minutes, the mixture was concentrated. The residue was dissolved in 3 ml of acetonitirile and after adding thereto 0.1 ml of tetrahydrofuran, the mixture was stirred for 5 minutes. The solution was added to another clear solution which was obtained by suspending 165 mg of 4-hydroxycarbamoylpyridine in 2 ml of acetonitrile and then adding 318 ml of bis(trimethylsilyl)trifluoroacetoamide.

The mixture was stirred for 5 hours at room temperature.

The reaction mixture was mixed with 0.1 ml of water and a crude product thus precipitated was collected by

EXAMPLE 13

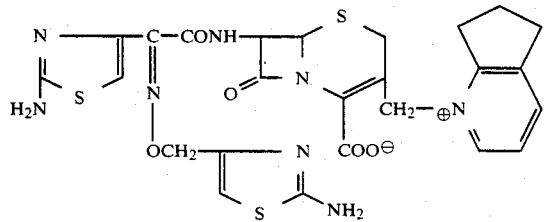

In 25 ml of dichloromethane was suspended 3.92 g of (Z)-α-(2-tritylamino-4-thiazolyl)-α-[(2-tritylamino-4-thiazolyl)methoxyimino]acetic acid and after cooling the suspension to 3° to 4° C. and adding thereto 1.04 g of phosphorus pentachloride, the mixture was stirred for 15 minutes at 3°-4° C. to provide Solution A. On the other hand, a solution containing trimethylsilyl 7-trimethylsilylamino-3-(2,3-cyclopenteno-1-pyridiniomethyl)-3-cephem-4-carboxylate iodide obtaining by Reference Example 2 was cooled to −50° C., and 2.2 ml of pyridine was added thereto to provide Solution B.

Solution A was added dropwise to solution B and the temperature of the reaction mixture was increased upto −15° C. over a period of 15 minutes. After adding to the reaction mixture 5 ml of water, 10 ml of tetrahydrofuran and 10 ml of 1N-hydrochloric acid, the mixture was stirred for 10 minutes under ice-cooling. The reaction mixture was distilled under reduced pressure to remove dichloromethane and tetrahydrofuran and after adding to the residue obtained 200 ml of water, precipitates thus formed were collected by filtration, washed with water, and dried to provide 5.5 g of a crude product (a compound having protective group). After adding to the crude product 60 ml of trifluoroacetic acid and 12 ml of water under ice-cooling, the mixture was stirred for 90 minutes at room temperature. Insoluble matters were removed by filtration, and the filtrate was concentrated under reduced pressure. To the residue was added 150 ml of ether to form a powder, and the powder was collected by filtration to provide 2.7 g of a crude product. The crude product was suspended in 200 ml of water and after adding 4 ml of 1N-hydrochloric acid to the formed suspension in order to dissolve the suspension, the formed solution was subjected to column chromatography on Diaion HP-20 and the product was eluted first with water and then with mixtures of water-methanol while changing succesively the mixing ratio (water:methanol=from 10:1 to 10:6). The fractions containing the desired product were concentrated, and lyophilized to provide 275 mg of (Z)-7-{α-(2-amino-4-thiazolyl)-α-[(2-amino-4-thiazolyl)methoxyimino]acetamido}-3-(2,3-cyclopenteno-1-pyridiniomethyl)-3-cephem-4-carboxylate.

NMR(DMSO—d$_6$) δ:

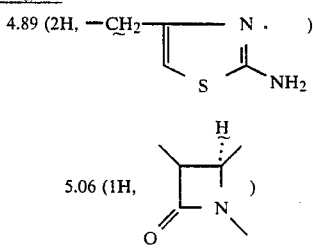

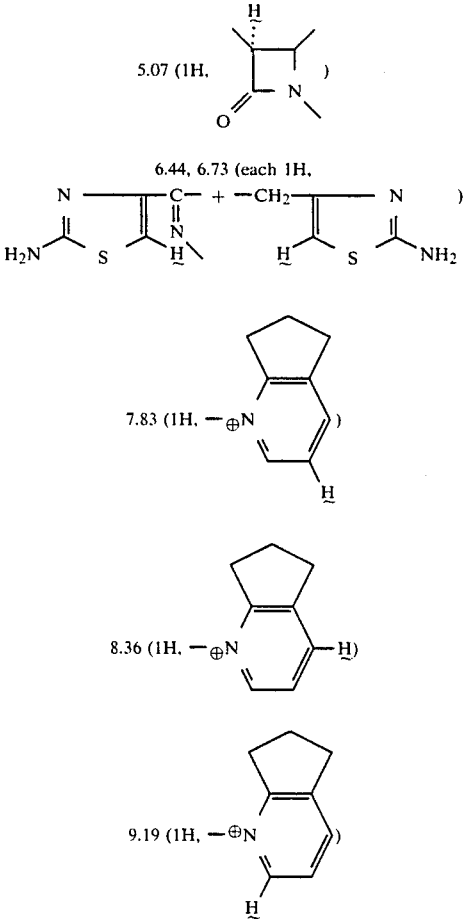

EXAMPLE 14

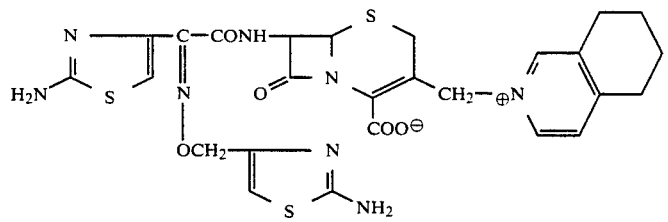

In 25 ml of dichloromethane was suspended 3.92 g of (Z)-α-(2-tritylamino-4-thiazolyl)-α-[(2-tritylamino-4-thiazolyl)methoxyimino]acetic acid and after cooling the suspension to 3° to 4° C. and adding thereto 1.04 g of phosphorus pentachloride, the mixture was stirred for 15 minutes at 3°∼4° C. to provide solution A. On the other hand, a solution containing trimethylsilyl 7-trimethylsilylamino-3-(5,6,7,8-tetrahydro-2-isoquinoliniomethyl)-3-cephem-4-carboxylate iodide obtained by Reference Example 3 was cooled to −50° C., and 2.2 ml of pyridine was added to the solution to provide solution B. Solution A was added dropwise to solution B and the temperature of the mixture was increased to −15° C. over a period of 15 minutes. To the solution were added 5 ml of water, 1N-hydrochloric acid, and 10 ml of tetrahydrofuran, and the resultant solution was stirred for 10 minutes under ice-cooling.

The reaction mixture was distilled under reduced pressure to remove dichloromethane and tetrahydrofuran and after adding to the residue obtained 200 ml of water, precipitates thus formed were collected by filtration to provide 10 g of a crude product containing water (a compound having protective groups). After adding to the crude product 70 ml of trifluoroacetic acid and 14 ml of water under ice-cooling, the mixture was stirred for 1 hour at room temperature. Insoluble matters were removed by filtration, and the filtrate was concentrated under reduced pressure. To the residue was added 200 ml of ether to form powder, and the powder was collected by filtration to provide 4 g of a crude product. The crude product was suspended in 300 ml of water and after adding 6 ml of 1N-hydrochloric acid to the formed suspension in order to dissolve the suspension, the formed solution was subjected to column chromatography on Diaion HP-20 and the product was eluted first with water and then mixtures of water and methanol while changing succesively the mixing ratio (water:-methanol=from 10:1 to 10:7). The fractions containing the desired product were concentrated, and lyophilized to provide 393 mg of (Z)-7-{α-(2-amino-4-thiazolyl)-α-[(2-amino-4-thiazolyl)methoxyimino]acetamido}-3-(5,6,7,8-tetrahydro-2-isoquinoliniomethyl)-3-cephem-4-carboxylate.

NMR (DMSO-d₆)

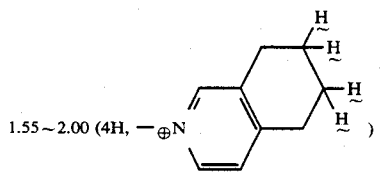

1.55~2.00 (4H, —⊕N )

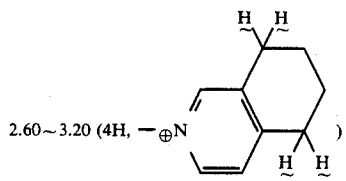

2.60~3.20 (4H, —⊕N )

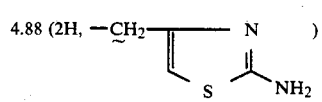

4.88 (2H, —CH₂— )

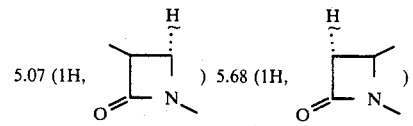

5.07 (1H, ) 5.68 (1H, )

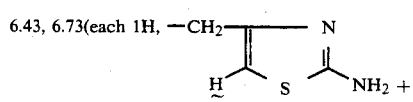

6.43, 6.73(each 1H, —CH₂— )

-continued

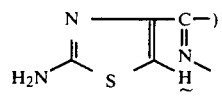

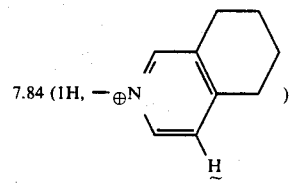

7.84 (1H, —⊕N )

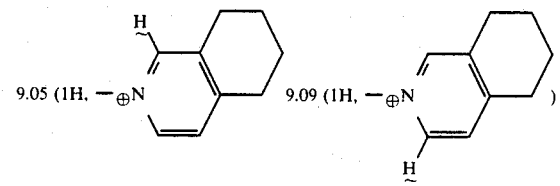

9.05 (1H, —⊕N )  9.09 (1H, —⊕N )

EXAMPLE 15

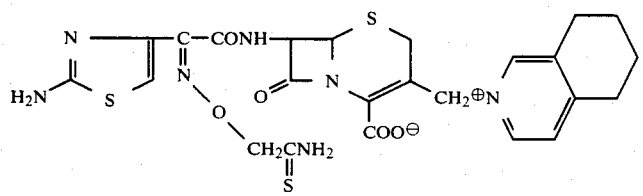

To 15 ml of dioxane were added 1.04 g (2 millimole) of (Z)-α-(thiocarbamoylmethoxyimino)-α-(2-tritylamino-4-thiazolyl)acetic acid, 297 mg (2.2 millimole) of 1-hydroxybenzotriazol and 450 mg (2.2 millimole) of dicyclohexylcarbodiimide and the mixture was allowed to react for 1 hour at room temperature. After the reaction is completed, dicyclohexylurea precipitated was removed by filtration, and a dioxane solution containing active ester obtained was distilled under reduced pressure to remove dioxane. To the formed residue was added 20 ml of dichloromethane to provide a dichloromethane solution containing the active ester. The solution was added at room temperature to a solution containing 2 millimole of trimethylsilyl 7-trimethylsilylamino-3-(5,6,7,8-tetrahydro-2-isoquinoliniomethyl)-Δ³-cephem-4-carboxylate iodide obtained by Reference Example 3. The mixture was allowed to react for 1 hour at room temperature, and thereafter distilled under reduced pressure to remove dichloromethane. To the formed residue were added 20 ml of water and 1.0 ml of 2N-hydrochloric acid solution and after stirring the mixture for 10 minutes at room temperature, the mixture was filtered to collect a crude product (2.15 g) of (Z)-7-[α-(2-tritylamino-4-thiazolyl)-α-(thiocarbamoylmethoxyimino)-acetamido]-3-(5,6,7,8-tetrahydro-2-isoquinoliniomethyl)-Δ³-cephem-4-carboxylate. The product was dissolved in 24 ml of trifluoroacetic acid under ice-cooling and after adding thereto 10 ml of water below 20° C., the mixture was allowed to react 1 hour at 19°–21° C. Insoluble matters were removed by filtration and the filtrate was concentrated under reduced pressure. To the formed residue was added 40 ml of ethanol, and the mixture was distilled to remove some amount of ethanol. To the formed residue was added 20 ml of ethyl ether to form powder, the powder was collected by filtration to provide 820 mg of a crude product.

The crude product was suspended in 5 ml of water and after adding 1 ml of 1N-hydrochloric acid to dissolve the suspension, the formed solution was subjected to column chromatography on Diaion HP-20 and the product was eluted first with water and then with mixtures of water and methanol while changing succesively the mixing ratio (volume ratio: water and methanol=-from 10:1 to 10:4). The fractions containing the desired product were concentrated and lyophilized to provide 56 mg of (Z)-7-[α-(2-amino-4-thiazolyl)-α-(thiocarbamoylmethoxyimino)acetamido]-3-(5,6,7,8-tetrahydro-2-isoquinoliniomethyl)-Δ³-cephem-4-carboxylate.

IR $\nu_{max}^{KBr}$ cm$^{-1}$;

3280~3330, 1770, 1670, 1610, 1530, 1380, 1330, 1030.

δ(ppm); NMR (d$_6$-DMSO)

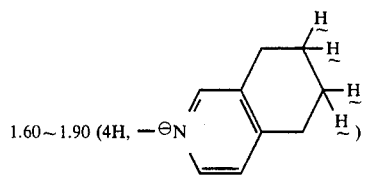

1.60~1.90 (4H, —⊖N     )

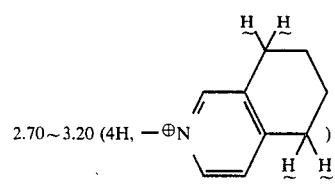

2.70~3.20 (4H, —⊕N     )

4.37 (2H, d, —CH$_2$—)   5.10 (1H, 6: CH)

5.49 (1H, 3: —CH$_2$—)   5.78 (1H, q, 7: CH)

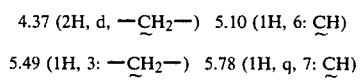

6.83 (1H, s, N     )

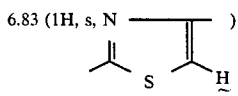

7.90 (1H, —⊕N     )

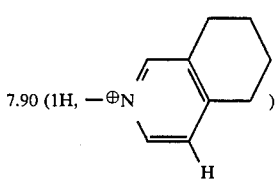

9.06 (1H, —⊕N     )

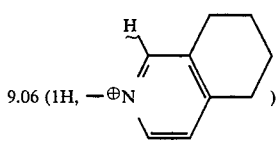

9.18 (1H, —⊕N     )   9.74 (1H, d, —CONH—)

EXAMPLE 16

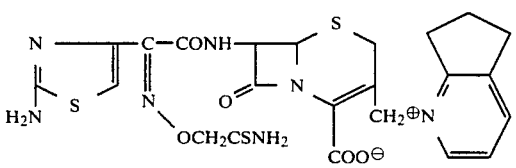

To 10 ml of dimethylformamide were added 260 mg (1 mM) of (Z)-α-(thiocarbamolymethoxyimino)-α-(2-amino-4-thiazolyl)acetic acid, 125 mg (1.1 mM) of 1-hydroxybenzotriazol, and 227 mg (1.1 mM) of dicyclohexylcarbodiimide, and the mixture was stirred for 1 hour at room temperature. Dicyclohexylurea precipitated was filtered away to provide a dimethylformamide solution of active ester. To the solution was added 257 μl of O,N-bis(trimethylsilyl)trifluoroacetamide. The mixture thus obtained was added at room temperature to another solution which contains 1.1 millimole trimethylsilyl 7-trimethylsilylamino-3-(2,3-cyclopneteno-1-pyridiniomethyl-Δ³-cephem-4-carboxylate iodide obtained by Reference Example 2. The mixture was stirred for 3 hours at room temperature and after adding thereto 1 ml of 1N-hydrochloric acid solution, the mixture formed was concentrated under reduced pressure. The residue thus obtained was powdered with ether and collected by filtration. 50 ml of water and 2 ml of 1N-hydrochloric acid solution were added thereto to form a suspension and the formed suspension was subjected to column chlomatography on Diaion HP-20 and the product was eluted first with water and then mixtures of water and methanol while changing succesively the mixing ratio (volume ratio; water:methanol=from 9:1 to 6:4). The fractions containing the desired product were concentrated and lyophilized to provide 87 mg of (Z)-7-[α-(2-amino-4-thiazolyl)-α-(thiocarbamoylmethoxyimino)acetamido]-3-(2,3-cyclopenteno-1-pyridiniomethyl)-Δ³-cephem-4-carboxylate.

IR$\nu_{max}^{KBr}$ cm$^{-1}$;
1765, 1665, 1610

NMR(d$_6$-DMSO) δ(ppm):

4.73 (2H, s, —CH$_2$—)
5.10 (1H, d, 6: —CH—)
5.38 (2H, q, 3: —CH$_2$—)
5.75 (1H, q, 7: —CH—)

NMR(d$^6$-DMSO⬜) δ(ppm):

3.34 (2H, q, 2: CH$_2$)
4.72 (2H, s, —OCH$_2$CS—)
5.14 (1H, d, 6: CH)
5.35 (2H, q, 3: —CH$_2$—)
5.79 (1H, q, 7: CH)

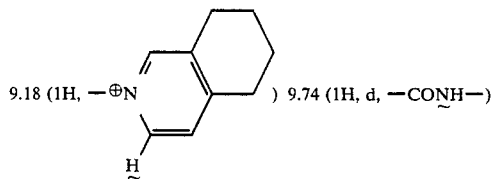

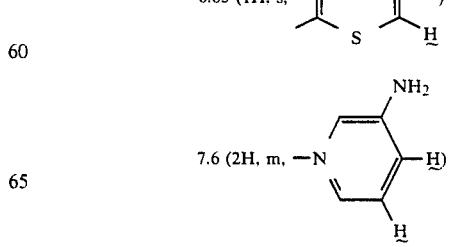

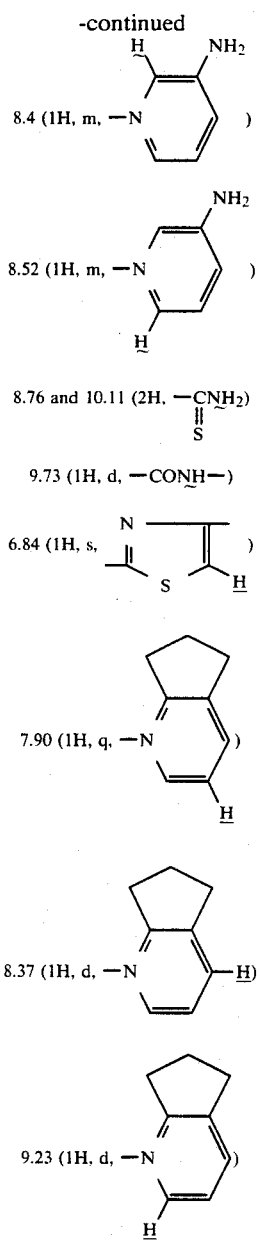

8.4 (1H, m, —N⟨⟩)

8.52 (1H, m, —N⟨⟩)

8.76 and 10.11 (2H, —CNH$_2$)
                        ‖
                        S 9.73 (1H, d, —CONH—)

6.84 (1H, s, ⟨⟩)

7.90 (1H, q, —N⟨⟩)

8.37 (1H, d, —N⟨⟩)

9.23 (1H, d, —N⟨⟩)

EXAMPLE 17

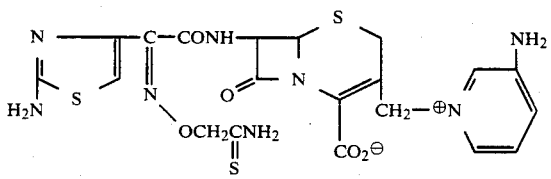

(i) In 1 ml of dimethylformamide was dissolved 73 mg of (Z)-α-(2-amino-4-thiazolyl)-α-thiocarbamoylmethoxyiminoacetic acid obtained by Reference Example 5. After adding thereto 38 mg of 1-hydroxybenzotriazol and 58 mg of dicyclohexylcarbodiimide, the mixture was allowed to react for 30 minutes at room temperature. After the reaction was over, dicyclohexylurea precipitated was filtered away to provide a dimethylformamide solution. To the solution was added 80 μl of O,N-bis(trimethylsilyl)trifluoroacetamide.

(ii) In 2 ml of dimethylformamide was dissolved 86 mg of 7-amino-3-(3-aminopyridiniomethyl)-Δ$^3$-cephem-4-carboxylate and 160 μl of O,N-bis(trimethylsilyl)-trifluoroacetamide was added thereto to form a pale yellow solution. To the solution was added another solution containing active ester obtained in the foregoing procedure mentioned at the above (i) and the mixture was allowed to react for 2 hours at room temperature. The reaction solution was concentrated under reduced pressure and after adding water and ethyl acetate to the residue, the aqueous layer was separated and subjected to column chromatography and the product was eluted with mixtures of water and methanol while changing succesively the mixing ratio. The fractions containing the desired product were concentrated to provide 35 mg of (Z)-7-[α-(2-amino-4-thiazolyl)-L60-(thiocarbamoylmethoxyimino)acetamido]-3-(3-aminopyridiniomethyl)-Δ$^3$-cephem-4-carboxylate.

IR $\nu_{max}^{KBr}$cm$^{-1}$;

3150 — 3450,1765,1650,1610,1525,1380,1340,1025

EXAMPLE 18

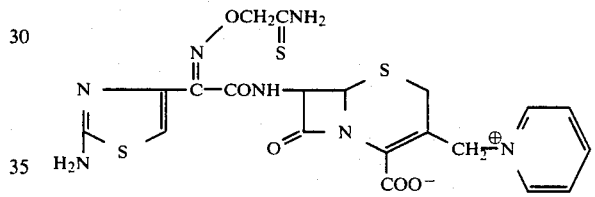

(i) In 10 ml of dichloromethane was suspended 360 g of 7-amino-3-pyridiniomethyl-Δ$^3$-cephem-4-carboxylic acid dihydrochloride and after adding thereto 1.55 ml of O,N-bis(trimethylsilyl)trifluoroacetamide, the mixture was stirred for 30 minutes at room temperature to form a clear solution.

(ii) To 10 ml of dioxane were added 550 mg of (Z)-α-(thiocarbamoylmethoxyimino)-α-(2-tritylamino-4-thiazolyl)-acetic acid, 150 mg of 1-hydroxybenzotriazol and 240 mg of dicyclohexylcarbodiimide, the mixture was reacted for 1 hour at room temperature. After the reaction was over, dicyclohexylurea precipitated was filtered away to provide a dioxane solution of active ester. Dioxane was distilled off under reduced pressure, and to the residue obtained was added 10 ml of dichloromethane to provide a dichloromethane solution of the active ester. The solution was added to another solution which was prepared in the above (i), and the mixture was reacted for 3 hours at room temperature. After the reaction was over, dichloromethane was distilled off under reduced pressure. To the residue thus formed was added 10 ml of water and 0.5 ml of 2N-hydrochloric acid, and the mixture was stirred for 10 minutes at room temperature. A crude product of (Z)-7-[α-(2-tritylamino-4-thiazolyl)-α-(thiocarbamoylmethoxyimino)acetamido]-3-pyridiniomethyl-Δ$^3$-cephem-4-carboxylate was collected by filtration. The crude product obtained was dissolved in 12 ml of trifluoroacetic acid under ice-cooling, and after adding thereto 3 ml of water below 20° C., the mixture was reacted for 1 hour at room temperature. The solvent was distilled off under reduced pressure and after adding to the residue ether to form powder, 0.58 g of a crude product was collected by filtration. The product was suspended in 20 ml of water and after adding thereto 1 ml of 1N-hydrochloric acid to dissolve the suspension, the solution was subjected to column chromatography on Diaion HP-20. The fractions containing the desired product were concentrated and lyophilized to provide 141 mg of (Z)-7-[α-(2-amino-4-thiazolyl)-α-(thiocarbamoylmethoxyimino)acetamido]-3-pyridiniomethyl-Δ³-cephem-4-carboxylate.

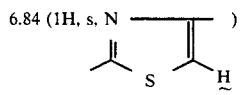

2800~3400, 1770, 1660, 1610, 1530, 1380, 1340, 1020,

NMR (d⁶-DMSO) δ(ppm); 3.35 (2H, q, 2: —$\underline{C}H_2$—)

4.72 (2H, s, —O$\underline{C}H_2$CS—)  5.10 (1H, 6: CH)

5.49 (2H, 3: —$\underline{C}H_2$—)  5.79 (1H, 7: CH)

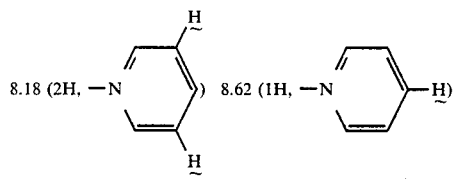

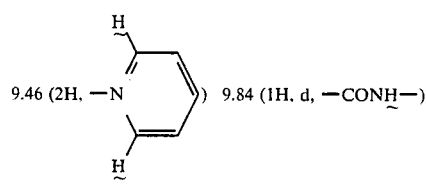

EXAMPLE 19

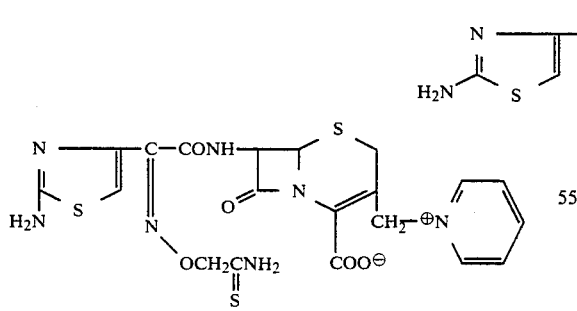

(i) In 20 ml of dichloromethane was suspended 680 mg of 7-amino-3-iodomethyl-Δ³-cephem-4-carboxylic acid and after adding thereto 1.2 ml of O,N-bis(trimethylsilyl)trifluoroacetamide, the mixture was stirred for 30 minutes at room temperature to provide a clear solution. To the solution was added 0.19 ml of pyridine and after stirring for 3 hours at room temperature, a solution containing trimethylsilyl 7-trimethylsilylamino-3-pyridiniomethyl-Δ³-cephem-4-carboxylate iodide was obtained.

(ii) On the other hand, 1.1 g of (Z)-α-(thiocarbamoylmethoxyimino)-α-(2-tritylamino-4-thiazolyl)acetic acid, 300 mg of 1-hydroxybenzotriazol and 480 mg of dicyclohexylcarbodiimide were added to 20 ml of dioxane, and the mixture was reacted for 1 hour at room temperature. After the reaction was over, dicyclohexylurea precipitated was filtered away to provide a dioxane solution of active ester. Dioxane was distilled off under reduced pressure and after adding 20 ml of dichloromethane to the formed residue, a dichloromethane solution of the active ester was obtained. The dichloromethane solution thus formed was added at room temperature to another solution containing trimethylsilyl 7-trimethylsilylamino-3-pyridiniomethyl-Δ³-cephem-4-carboxylate iodide obtained in the above (i). After the reaction was carried out for 3 hours at room temperature, dichloromethane was distilled away under reduced pressure. After adding to the residue formed 30 ml of water and 4 ml of 1N-hydrochloric acid to form powder, the powder was collected by filtration to provide 1.59 g of a crude product of (Z)-7-[α-(2-tritylamino-4-thiazolyl)-α-(thiocarbamoylmethoxyimino)acetamido]-3-pryridiniomethyl-Δ³-cephem-4-carboxylate. After adding thereto 20 ml of trifluoroacetic acid under ice-cooling, removing insoluble matters by filtration, and adding to the filtrate 8 ml of water below 20° C., the mixture was stirred for 1 hour at room temperature. After completing the reaction, concentrating the mixture under reduced pressure, and adding ether to the residue to form powder, the powder was collected to provide a crude product. After suspending the product thus obtained in 20 ml of water and then adding 1N-hydrochloric acid to dissolve the suspension, the solution was subjedted to column chromatorgraphy on Diaion HP-20 and the product was eluted with mixtures of water and methanol while changing succesively the mixing ration from 9:1 to 7:3. The fractions containing the desired product were collected, and concentrated, and lyophilized to provide 141 mg of (Z)-7-[α-(2-amino-4-thiazolyl)-α-(thiocarbamoylmethoxyimino)acetamido]-3-pyridiniomethyl-Δ³-cephem-4-carboxylate.

EXAMPLE 20

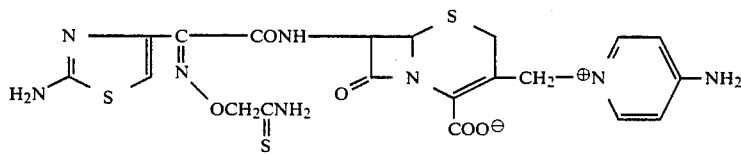

(i) In 15 ml of dichloromethane was suspended 510 mg of 7-amino-3-iodometyl-Δ³-cephem-4-carboxylic acid and after adding thereto 0.85 ml of O,N-bis(trimethylsilyl)-trifluoroacetamide and stirring the mixture for 30 minutes at room temperature, a clear solution was obtained. After adding 310 mg of 4-(t-butyloxycarbonylamino)pyridine to the solution obtained, the mixture was stirred for 3.5 hours at room temperature to provide a solution containing trimethylsilyl 7-trimethylsilylamino-3-[4-(t-butyloxycarbonylamino)pyridiniomethyl]-Δ³-cephem-4-carboxylate iodide.

(ii) To 15 ml of dioxane were added 753 mg of (Z)-α-(thiocarbamoylmethoxyimino)-α-(2-tritylamino-4- thiazolyl)acetic acid, 203 mg of 1-hydroxybenzotriazol, and 310 mg of dicyclohexylcarbodiimide, and the reaction was carried out for 1 hour at room temperature. After the reaction was over, dicyclohexylurea precipitated was filetered away to provide a dioxane solution of active ester. Dioxane was distilled off under reduce pressure and after adding 10 ml of dichloromethane to the formed residue, a dichloromethane solution of the active ester was obtained. The dichloromethane solution thus obtained was added at room temperature to another solution containing trimethylsilyl 7-trimethylsilylamino-3-[4-(t-butyloxycarbonylamino)pyridiniomethyl]-Δ³-cephem-4-carboxylate iodide obtained in the above (i). The mixture was reacted for 4 hours at room temperature and after adding thereto 2 ml of tetrahydrofuran and 1 ml of water, and stirring the mixture for 10 minutes at the same temperature, the formed mixture was concentraed under reduced pressure. To the residue was added 10 ml of ethyl acetate to form powder, and the powder was collected by filtration to obtain 1.15 g of a crude product of (Z)-7-[α-(2-tritylamino-4-thiazolyl)-α-(thiocarbamoylmethoxyimino)acetamido]-3-[4-(t-butyloxycarbonylamino)pyridiniomethyl]-Δ³-cephem-4-carboxylate. The product was dissolved under ice-cooling in a mixture of 5 ml of anisole and 10 ml of trifluoroacetic acid and after performing the reaction for 1 hour at room temperature, the reaction mixture was concentrated under reduced pressure. To the resiudue was added ether to form powder, and the powder was collected by filtration. To the powder thus obtained was added under ice-cooling 15 ml of trifluoroacetic acid and 5 ml of water, and the mixture was reacted for 1 hour at room temperature. After removing insoluble matter by filtration, concentrating the filtrate under reduced pressure, and adding ether to the formed residue to form powder, the powder was collected by filtration to obtain 620 mg of a crude product. To the product were added 20 ml of water and 1 ml of 1N-hydrochloric acid to dissolve the product, the solution formed was subjected to column chromatography on Diaion HP-20. Fractions containing the desired product were collected, concentrated, and lyophilized to provide 71.4 mg of (Z)-7-[α-(2-amino-4-thiazolyl)-α-(thiocarbamoylmethoxyimino)acetamido]-3-(4-aminopyridiniomethyl)-Δ³-cephem-4-carboxylate.

IR $\nu_{max}^{KBr}$ cm$^{-1}$;

1760, 1650, 1600, 1530, 1350, 1160, 2800~3550
NMR (d⁶-DMSO) δ(ppm);
3.26 (2H, q, 2: —CH₂—)
4.54 (2H, —OCH₂CSNH₂)
5.12 (1H, 6: CH)
5.66 (1H, 7: CH)

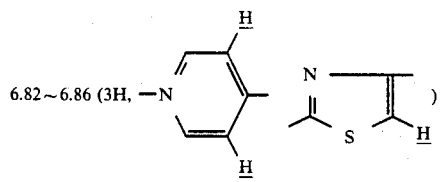

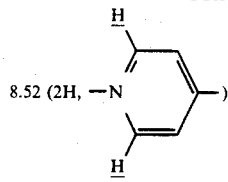

EXAMPLE 21

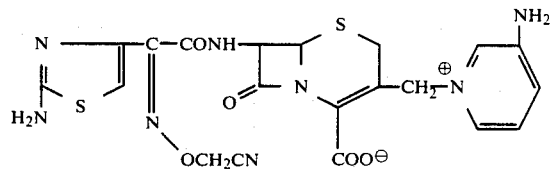

In 4 ml of dichloromethane was suspended 377 mg of (Z)-α-(2-tritylamino-4-thiazolyl)-α-cyanomethoxyiminoacetic acid and after adding thereto 166 mg of phosphorus pentachloride under ice-cooling, the mixture was stirred fro 30 minutes to provide solution A.

On the other hand, in 10 ml of dichloromethane was suspended 340 mg of 7-amino-3-iodomethyl-Δ³-cephem-4-carboxylic acid and after adding thereto 0.56 ml of N,O-bis(trimethylsilyl)trifluoroacetamide, the mixture was stirred for 30 minutes at room temperature to provide solution B.

On the other hand, in 1 ml of dichloromethane was dissolved 94 mg of 3-aminopyridine and after adding thereto 0.27 ml of N,O-bis(trimethylsilyl)trifluoroacetamide, the mixture was stirred for 5 minutes at room temperature to provide solution C.

Solution C was added to Solution B, and the mixture was stirred for 5 hours at room temperature. After cooling the reaction mixture thus formed to —40° C. and adding thereto 0.32 ml of pyridine and adding further thereto Solution A, the temperature of the mixture was increased to —15° C. over a period of 30 minutes. T the reaction mixture were added 2 ml of tetrahydrofuran and 2 ml of 1-hydrochloric acid, and the mixture was stirred for 10 minutes under ice-cooling. The solvent was distilled off under reduced pressure and after adding 20 ml of water to the formed residue, precipitates thus formed were collected by filtration.

The precipitates thus obtained were washed with water and dried to provide 420 mg of a crude product (a compound having protective group). To the crude product were added under ice-cooling 10 ml of trifluoroacetic acid and 5 ml of water, and the mixture was stirred for 1 hour at room temperature. Insoluble matters were removed by filtration and after concentrating the filtrate under reduced pressure and adding to the formed residue 50 ml of ether to powder the residue, the powder was collected by filtration to provide 190 mg of a crude product. The product was suspended in 50 ml of water and after adding thereto 1N-hydrochloric acid to adjust the pH of the mixture to 2, the mixture was subjected to column chromatography on Diaion HP-20 and the product was eluted first with water and then mixtures of water and methanol while changing the mixing ratio succesively from 9:1 to 7:3. Fractions containing the desired product were collected, concentrated, and lyophilized to provide 17 mg of (Z)-7-[α-(2-amino-4- thiazolyl)-α-cyanomethoxyiminoacetamido]-3-(3-amino-1-pyridiniomethyl)-Δ³-cephem-4-carboxylate.

NMR (DMSO—d₆)
δ(ppm)4.94 (2H, —CH₂CN)

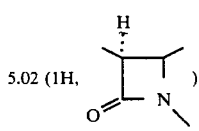
5.02 (1H,

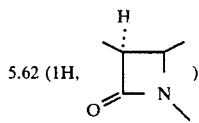
5.62 (1H,

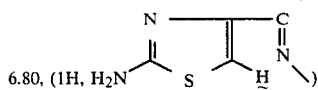
6.80, (1H, H₂N

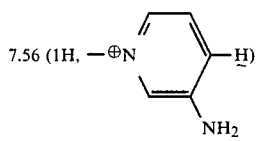
7.56 (1H, —⊕N

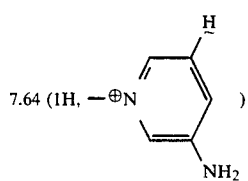
7.64 (1H, —⊕N

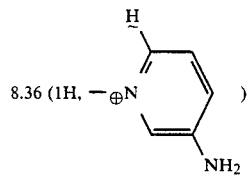
8.36 (1H, —⊕N

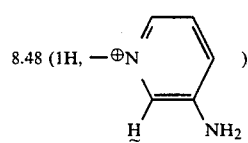
8.48 (1H, —⊕N

We claim:

1. A cephalosporin compound of the following formula, or a pharmaceutically acceptable nontoxic salt thereof:

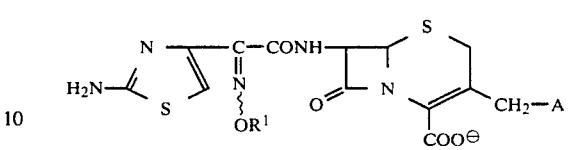

wherein the wavy line means syn-form and anti-form bonds, R¹ represents an aminothiaxolylmethyl group, and A represents

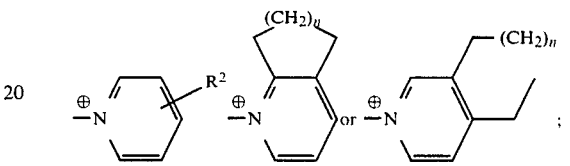

in the above formulas, n represents an integer of 1 to 2, R² represents a hydrogen atom, a sulfo group, —(CH₂)$_m$COOH, —(CH₂)$_m$OH, —(CH₂)mNHR³, or —CONHR⁴; in these formulas, m represents 0 or an or an integer of 1 to 3, R³ represents a hydrogen atom or a formyl, acetyl, propionyl or oxalo group, and R⁴ represents a carboxy lower alkyl group or a hydroxyl group.

2. The syn isomer of a compound according to claim 1.

3. The anti isomer of a compound according to claim 1.

4. A compound according to claim 1 wherein A is an aminopyridinio group, and R¹ is an aminothiazolylmethyl group.

5. A compound according to claim 1 wherein A is a 3-aminopyridinio group, and R¹ is a 2-aminothiazolylmethyl group.

6. A compound according to claim 1 wherein A represents a 2,3-cyclopenteno-1-pyridinio group, and R¹ represents a 2-aminothiazolylmethyl group.

7. A compound according to claim 1 wherein A represents a 3-aminopyridinio group.

8. A compound according to claim 1 wherein the lower alky group is a straight or branched carbon chain alkyl having 1 to 4 carbon atoms.

9. A compound according to claim 1, wherein R¹ is an aminothiazolylmethyl group.

* * * * *